(12) United States Patent
Chattipakorn et al.

(10) Patent No.: US 6,246,908 B1
(45) Date of Patent: Jun. 12, 2001

(54) METHOD AND APPARATUS FOR RAPIDLY PREDICTING OUTCOME OF ARRHYTHMIA THERAPY

(75) Inventors: Nipon Chattipakorn; Raymond E. Ideker, both of Birmingham, AL (US); Bruce H. KenKnight, Maple Grove, MN (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/498,898

(22) Filed: Feb. 4, 2000

(51) Int. Cl.$^7$ .................................................. A61N 1/39
(52) U.S. Cl. ............................................................ 607/5
(58) Field of Search .................................. 607/4, 5, 6, 7, 607/8, 14

(56) References Cited

U.S. PATENT DOCUMENTS

| | | | |
|---|---|---|---|
| 5,978,704 | 11/1999 | Ideker et al. | 607/5 |
| 5,978,705 | 11/1999 | KenKnight | 607/5 |
| 5,987,354 | 11/1999 | Copper et al. | 607/5 |
| 6,006,131 | 12/1999 | Cooper et al. | 607/5 |

OTHER PUBLICATIONS

Walker et al.; *Abstract 738–2–Postshock Epicardial Activation Patterns Predict Outcome of Attempted Defibrillation*, JACC Abstracts—Oral, 147A (1996).

Hamer et al.; *Factors Related to the Induction of Ventricular Fibrillation in the Normal Canine Heart by Programmed Electrical Stimulation*, JACC, 3(3):751–759 (1984).

*Primary Examiner*—Scott M. Getzow
(74) *Attorney, Agent, or Firm*—Myers Bigel Sibley & Sajovec

(57) ABSTRACT

A method for predicting the outcome of arrhythmia therapy in a subject in need thereof comprises the steps of: (a) detecting an arrhythmia in the heart of a subject; (b) delivering a first arrhythmia therapy pulse to the heart of the subject; and then (c) determining the presence or absence of overlapping cycles in the heart of the subject, the presence of overlapping cycles indicating that the first arrhythmia therapy pulse did not successfully treat the arrhythmia. Overlapping cycles are preferably determined through the calculation of an overlapping cycles index (OCI). Apparatus for carrying out the method is also disclosed.

33 Claims, 22 Drawing Sheets

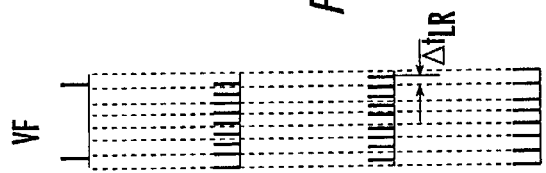
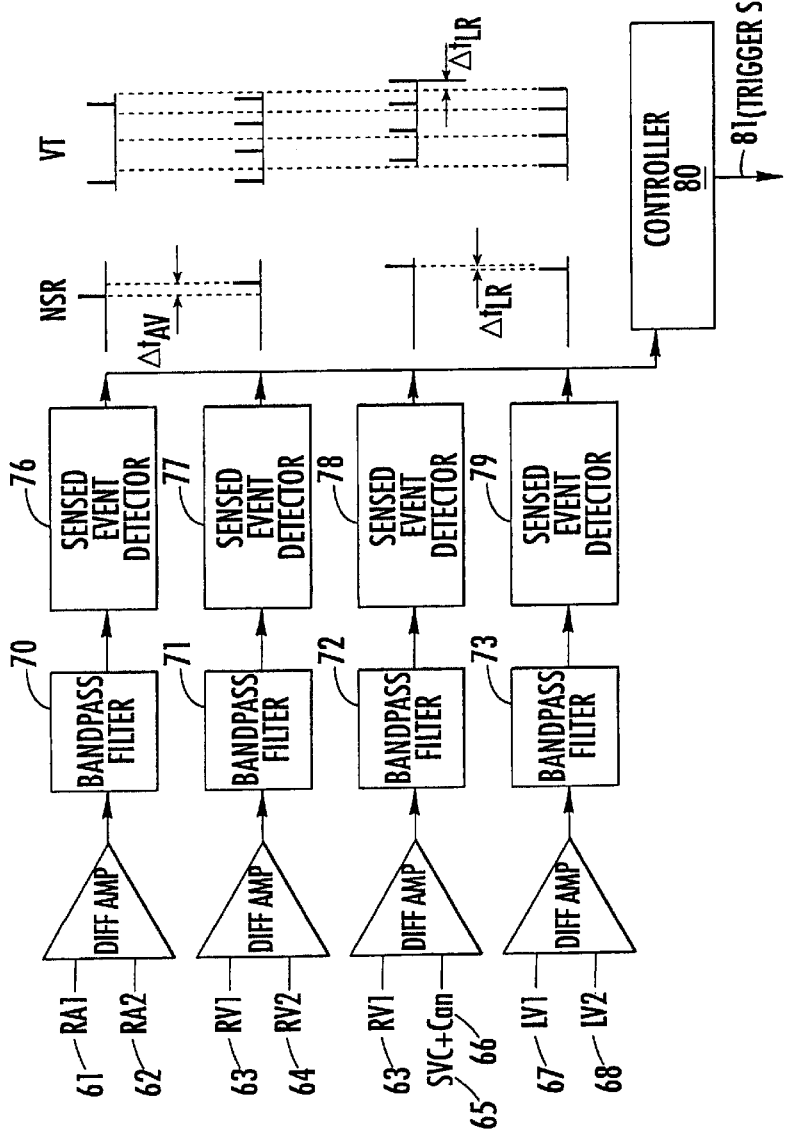

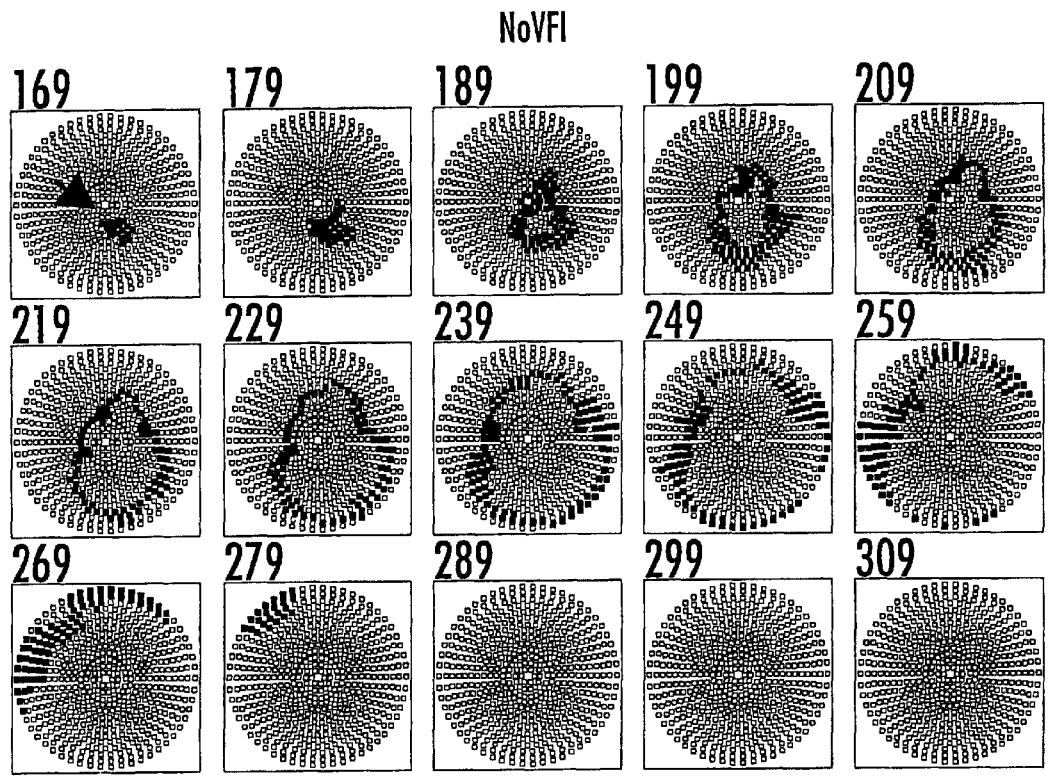
FIG. 8B1.
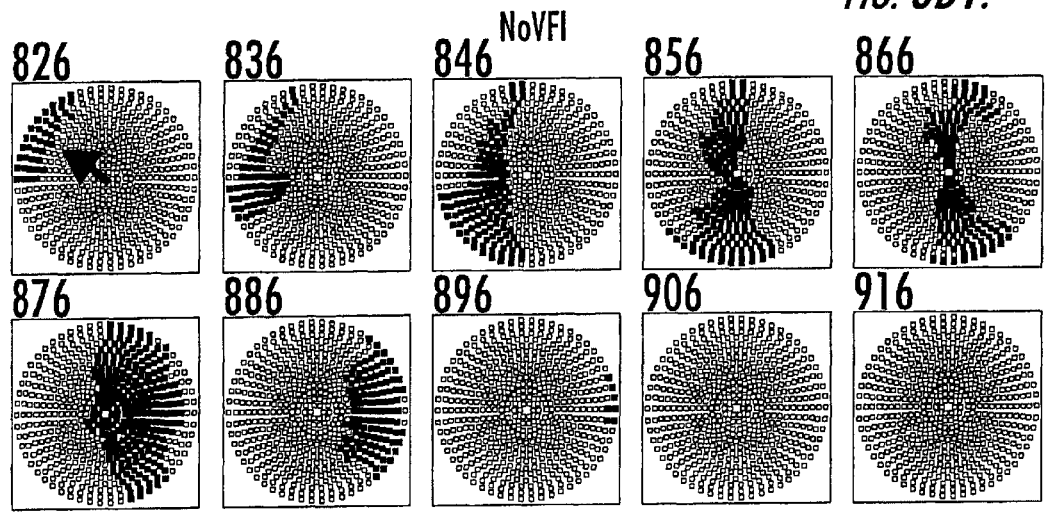
FIG. 8B2.
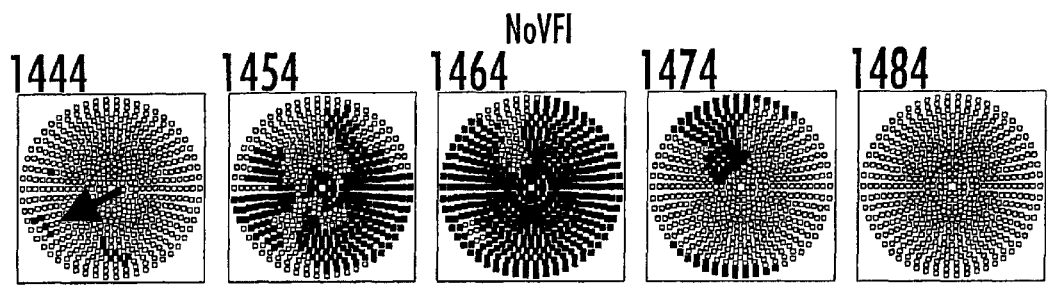
FIG. 8B3.

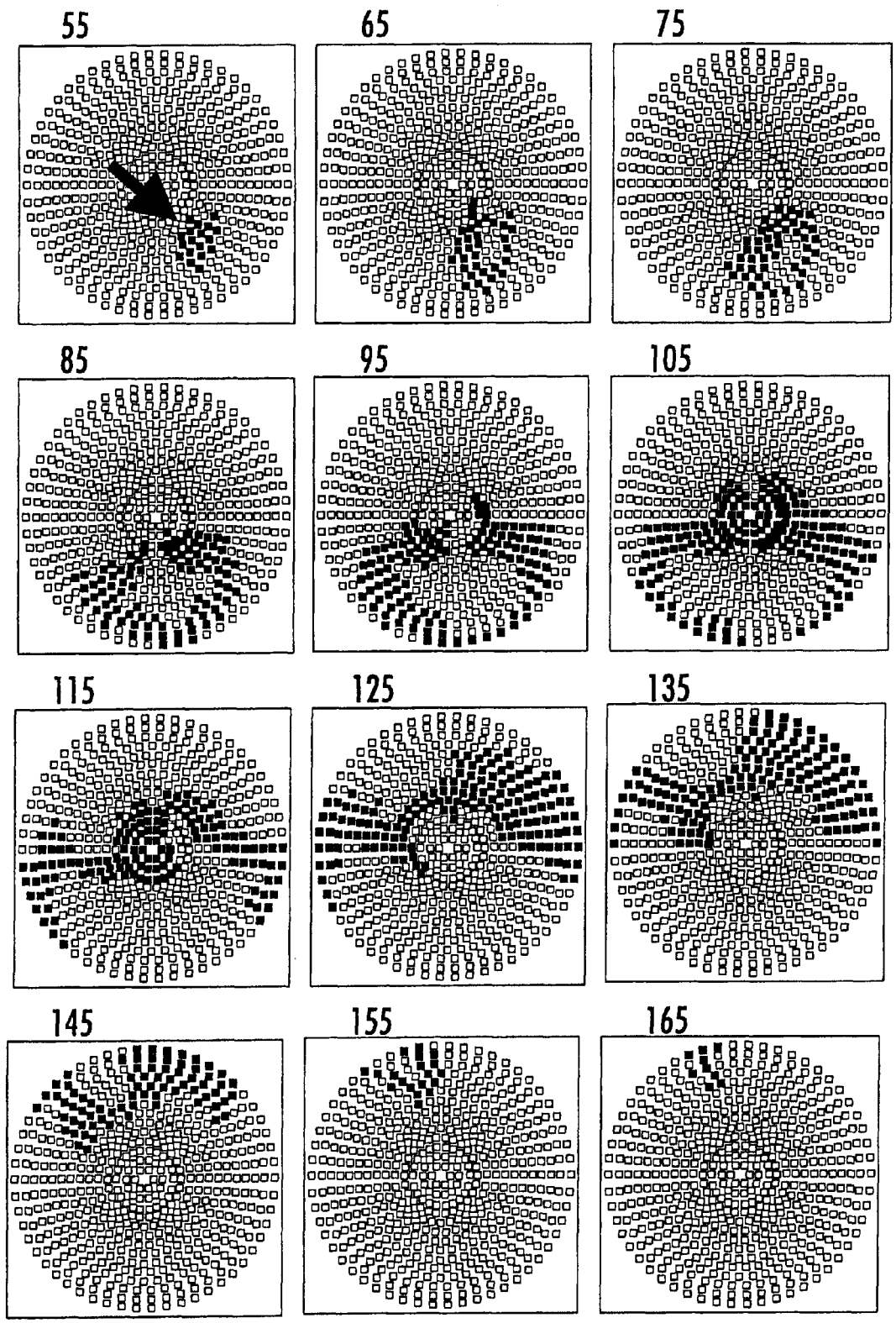
FIG. 11A1.

FIG. 11B1.
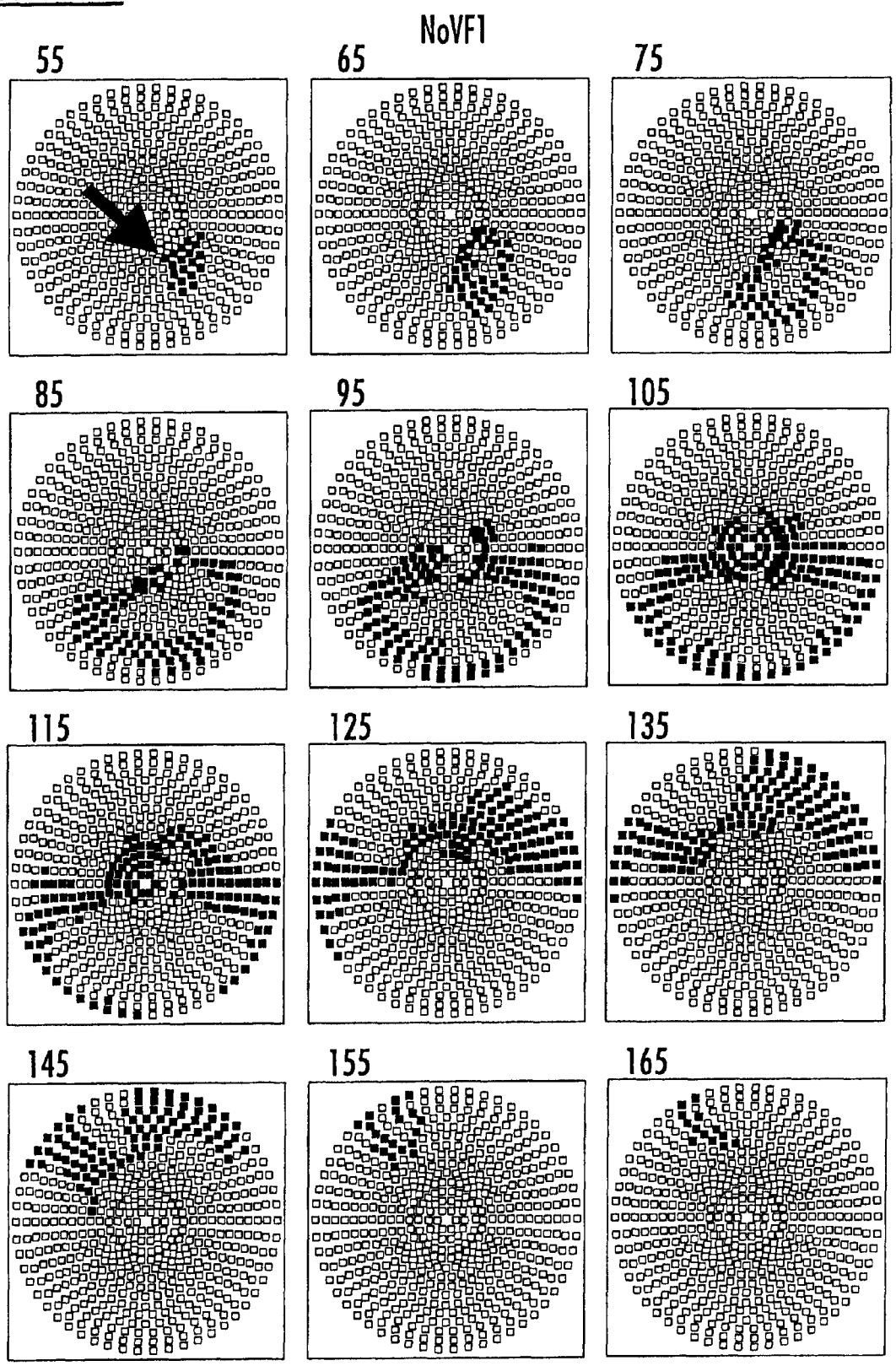

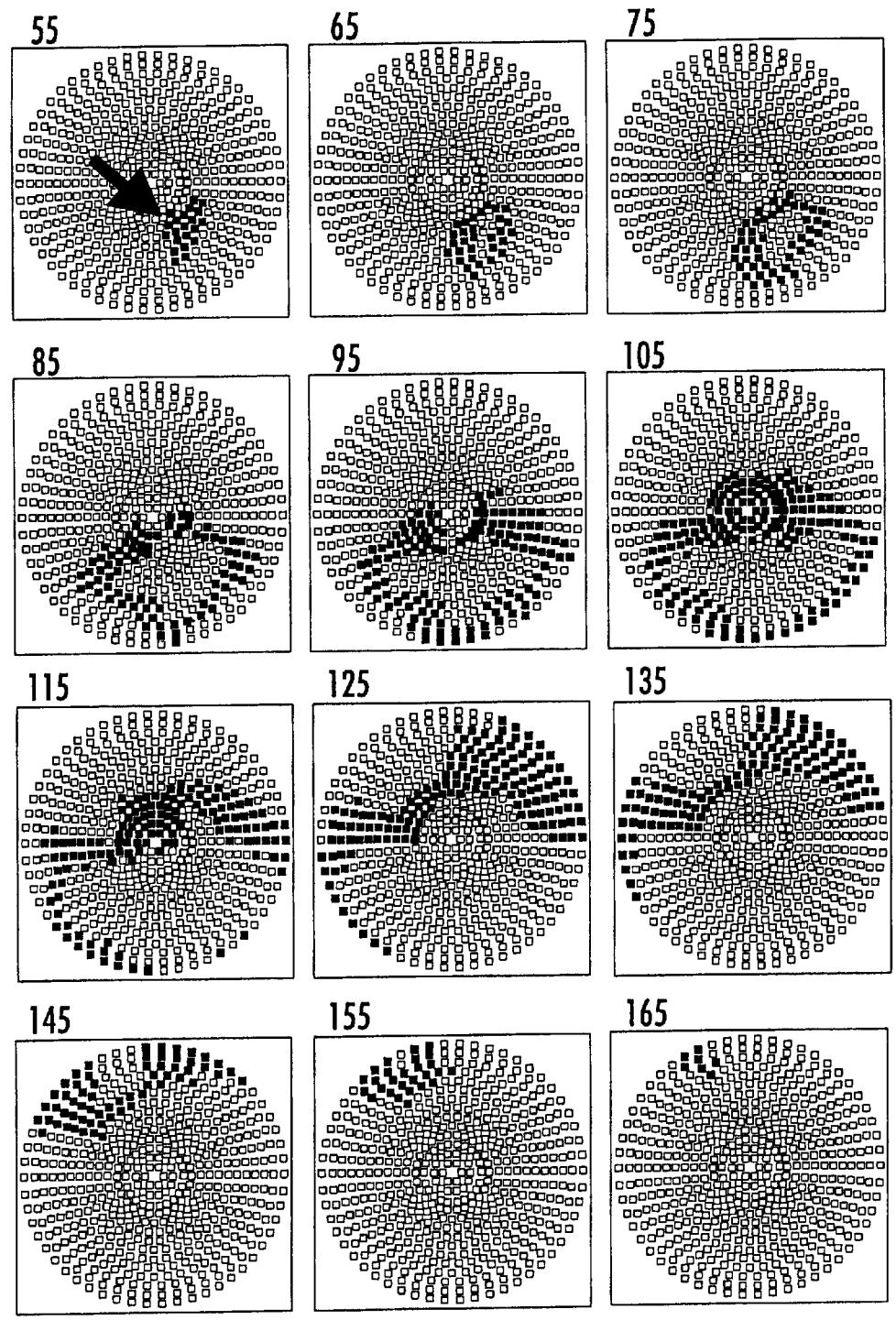
FIG. 11C1.

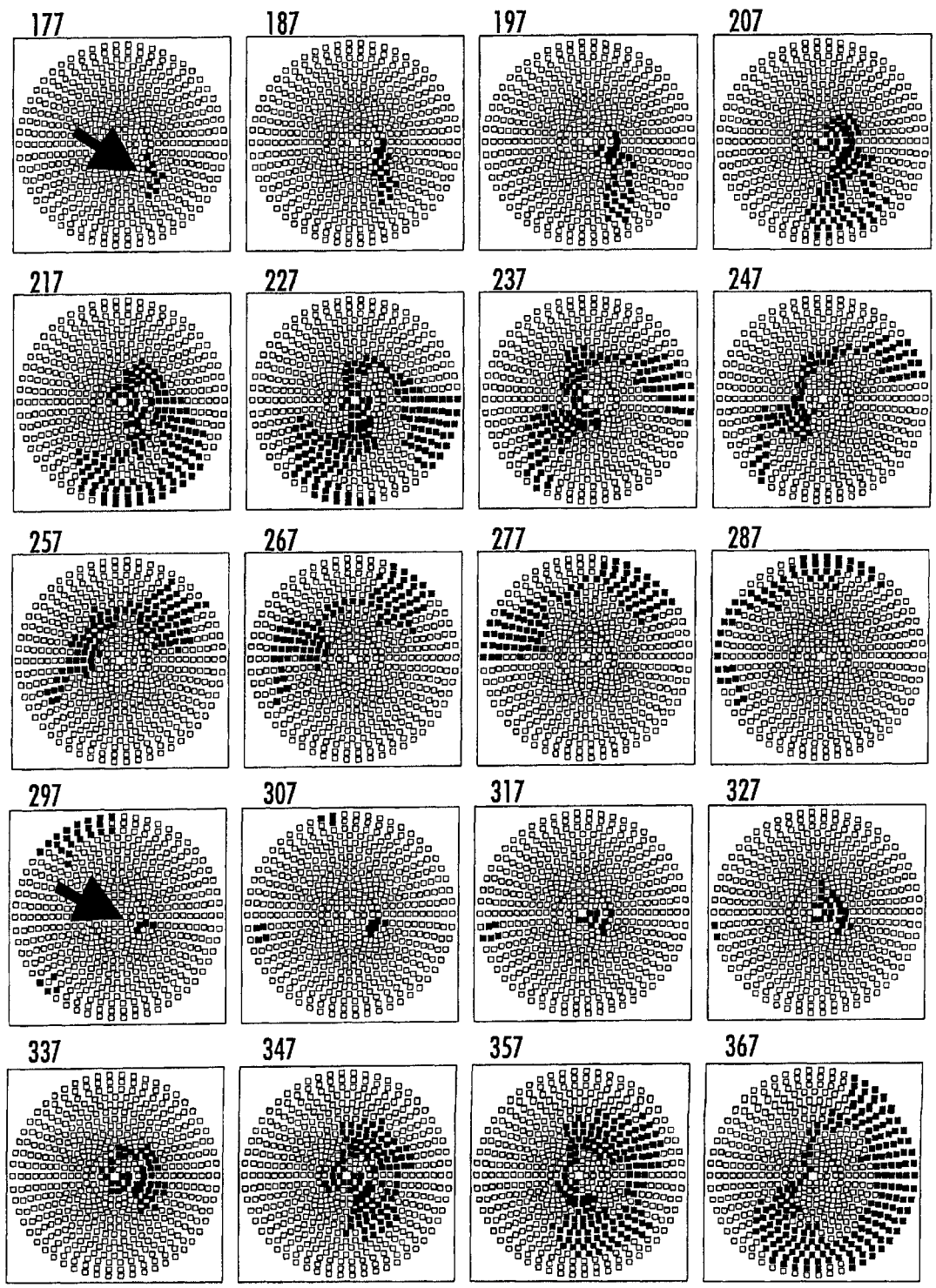
FIG. 11A2.

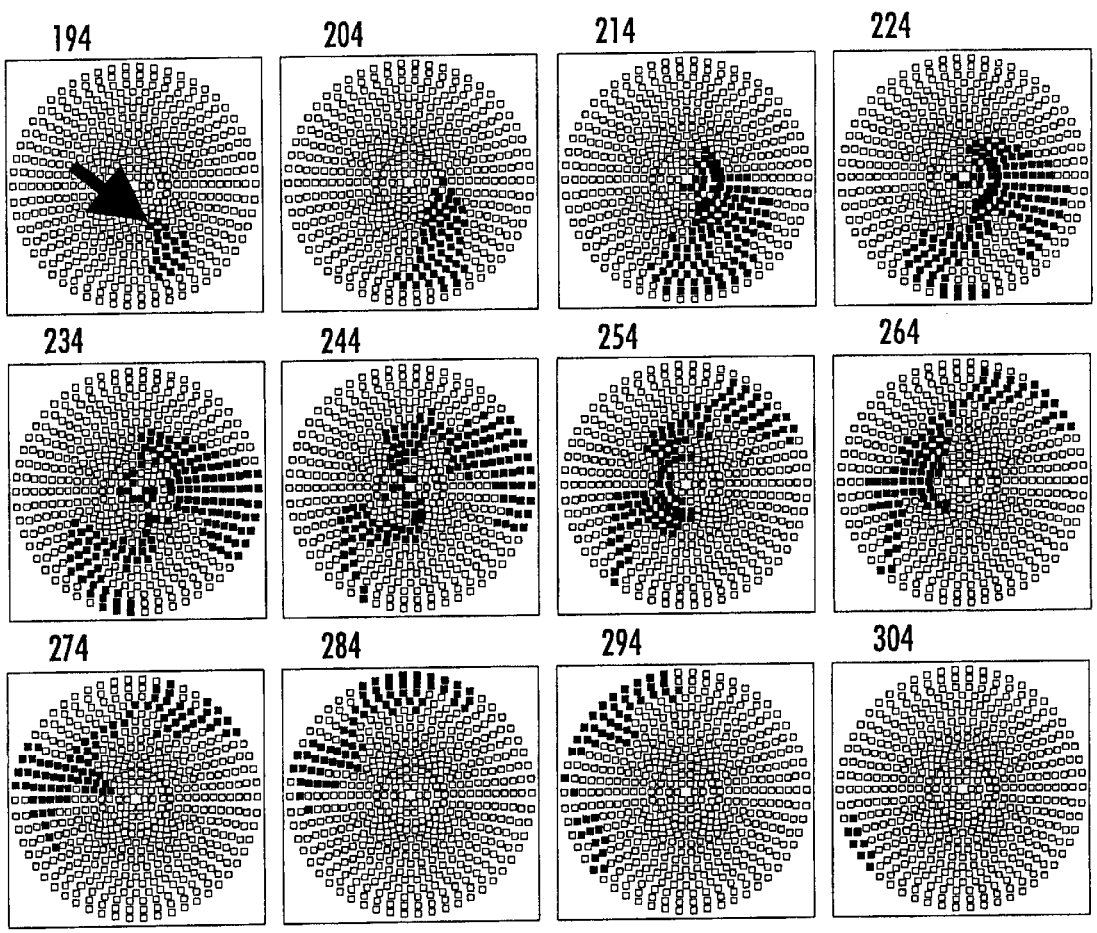
FIG. 11B2.

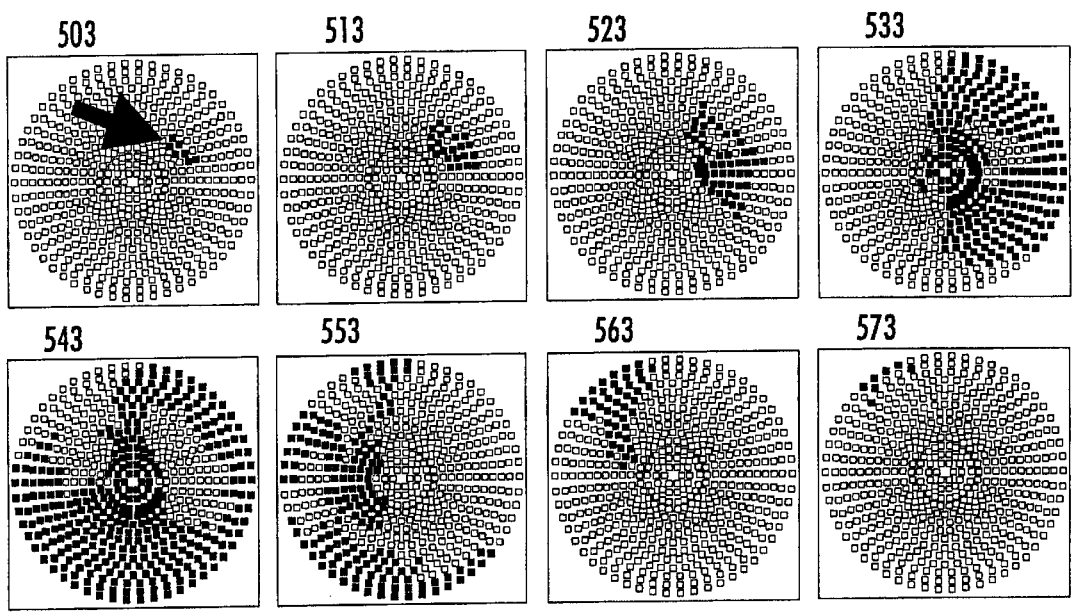
FIG. 11C2.

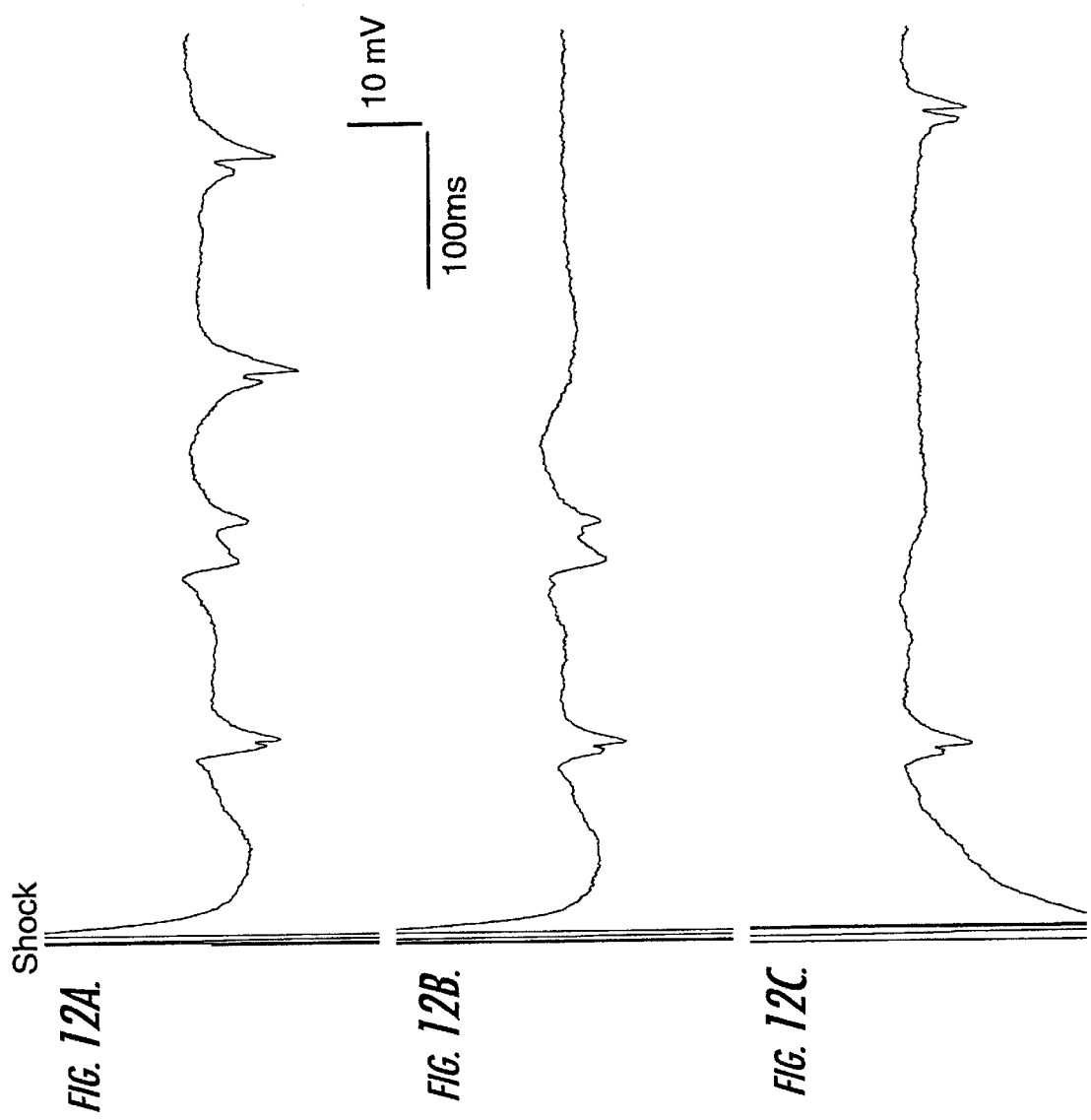

METHOD AND APPARATUS FOR RAPIDLY
PREDICTING OUTCOME OF ARRHYTHMIA
THERAPY

This invention was made with Government support under National Institutes of Health research grants HL-28429 and HL-42760. The Government has certain rights to this invention.

FIELD OF THE INVENTION

The present invention relates to methods and apparatus for rapidly predicting the success or failure of an arrhythmia therapy pulse or shock to the heart of a subject, so that the need for an additional or alternate therapy pulse can be more rapidly determined and such pulse, if necessary, then delivered.

BACKGROUND OF THE INVENTION

Since defibrillation is probabilistic and shock strength dependent, shocks of the same strength sometimes succeed and other times fail (Davy J M et al, *Am. Heart J.* 1987;113:77–84). It would be very useful if there were a way to predict defibrillation outcome soon after the shock so that the rescue shock could be delivered quickly with less time spent in ventricular fibrillation (VF) (Weaver W D et al, *Journal of the American College of Cardiology* 1986;7:752–7; Echt D S et al, Pacing and *Clin. Electrophys.* 1988;11:1315–1323).

Several studies have investigated activation before and after successful and failed shocks to try to predict defibrillation outcome. Those studies that used different shock strengths focused on the observation that the postshock interval (i.e. the interval between the shock and the first postshock activation) can be used to predict the shock outcome. In these studies the shock strengths for successful episodes were generally higher than for the failed episodes. Other studies that used the same shock strength for both successful and failed episodes did not find this relationship. Despite this controversy, all studies agree that, following shocks near the defibrillation threshold, a few organized ectopic cycles of activation occur prior to degeneration into VF for failed shocks or return to sinus rhythm for successful shocks. (Chen P -S, et al.: *J. Clin. Invest.* 1986;77:810–823; Shibata N et al: *Am. J Physiol.* 1988;255: H902–H909; Tovar O H and Jones J L: *Am. J Physiol.* 1997;272: H1011–H1019; Zhou X, et al.: *Circ. Res.* 1993;72:145–160; Usui M, et al: *J Cardiovasc. Electrophysiol.* 1996;7:322–334). Hence, there remains a need for new ways to predict defibrillation outcome promptly after the delivery of a cardiac therapy pulse.

SUMMARY OF THE INVENTION

A first aspect of the present invention is a method for predicting the outcome of arrhythmia therapy in a subject in need thereof. The method comprises the steps of: (a) detecting an arrhythmia in the heart of a subject; (b) delivering a first arrhythmia therapy pulse to the heart of the subject; and then (c) determining the presence or absence of overlapping cycles in the heart of the subject, the presence of overlapping cycles indicating that the first arrhythmia therapy pulse did not successfully treat the arrhythmia. The determining step is preferably carried out within the first 3, 5 or 10 cardiac cycles (inclusive) following the arrhythmia therapy pulse (and preferably within about one second of the first arrhythmia therapy pulse). The method then preferably further comprises the step of: (d) delivering a second arrhythmia therapy pulse if overlapping cycles are determined. The method can be used to treat any of a variety of different atrial and ventricular arrhythmias, particularly atrial and ventricular fibrillation.

While the determining step described above may be carried out by any suitable means, it is preferably carried out by calculating an overlapping cycle index. The overlapping cycle index may be calculated from the wavefront conduction time of a given cycle and the intercyle interval of the cycle subsequent to the given cycle. Preferably, the given cardiac cycle is within the first 2, 4, 9 or 10 cycles following the first arrhythmia therapy pulse. Thus, the determining step is carried out within the first 3, 5 10 or 11 cardiac cycles following the first arrhythmia therapy pulse.

A second aspect of the present invention is an apparatus for delivering an arrhythmia therapy pulse to a subject in need thereof and rapidly predicting the outcome of the arrhythmia therapy. The apparatus comprises: (a) a detector for detecting an arrhythmia in the heart of a subject; (b) a therapy pulse generator (e.g., a battery and capacitor circuit with suitable control circuitry) operatively associated with the detector for delivering a first arrhythmia therapy pulse to the heart of the subject; and (c) a microprocessor, control circuit or the like, which may be implemented in hardware, software, or both hardware and software, providing for determining means for determining the presence or absence of overlapping cycles in the heart of the subject following the first arrhythmia therapy pulse, the presence of overlapping cycles indicating that the first arrhythmia therapy pulse did not successfully treat the arrhythmia. Control circuitry or other suitable triggeringmeans may be operatively associated with the determining means and the therapy pulse generator for triggering the delivery of a second arrhythmia therapy pulse by the therapy pulse generator if overlapping cycles are detected.

The apparatus is preferably an implantable cardioverter defibrillator (ICD). Thus the apparatus typically includes a housing, with the detector, the therapy pulse generator, and the determining means contained within the housing. A defibrillation electrode may be formed on the outer surface of the housing to provide an "active can" electrode.

The foregoing and other objects and aspects of the invention are described in the drawings herein and the specification set forth below.

The 504-electrode elastic sock extended above the AV groove. Panel C: The biphasic waveform consisted of a 6-ms first phase and a 4-ms second phase with 0.2-ms interphase delay. Panel D: A polar projection displayed dV/dt at all electrode sites (squares). Ao=aorta, LAD=left anterior descending coronary artery, LV=left ventricle, PA=pulmonary artery, RA=right atrium, RV=right ventricle, RVB=right ventricular base, LVB=left ventricular base, SVC=superior vena cava.

Figure 6A:
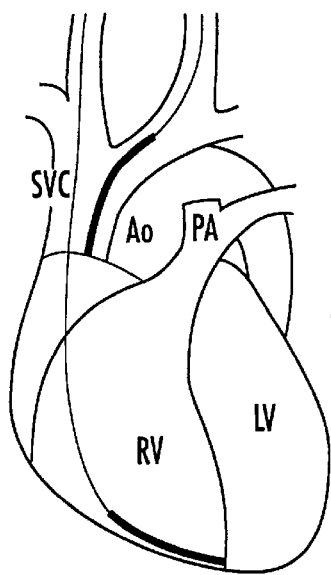
FIG. 6: Shocking electrode (S2) configuration and mapping array in experimental pigs. Panel A: Shocking electrodes were positioned at the SVC and RV apex. Pacing stimuli (S1) were delivered from the catheter tip. Panel B.
Figure 6D:
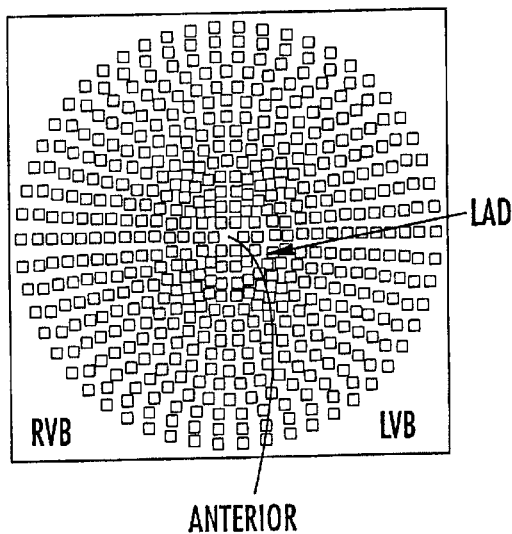
Figure 7A:
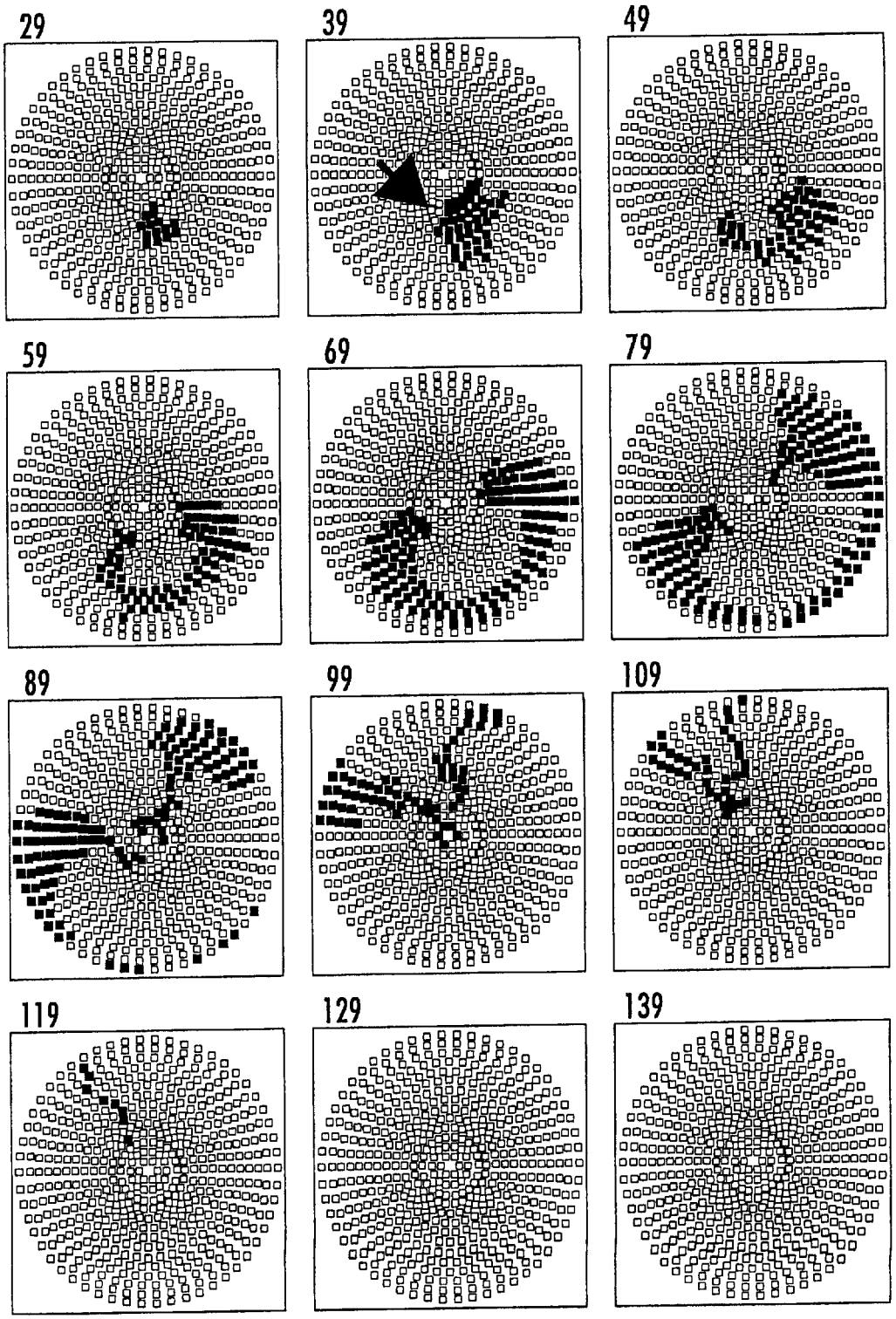
Figure 7B:
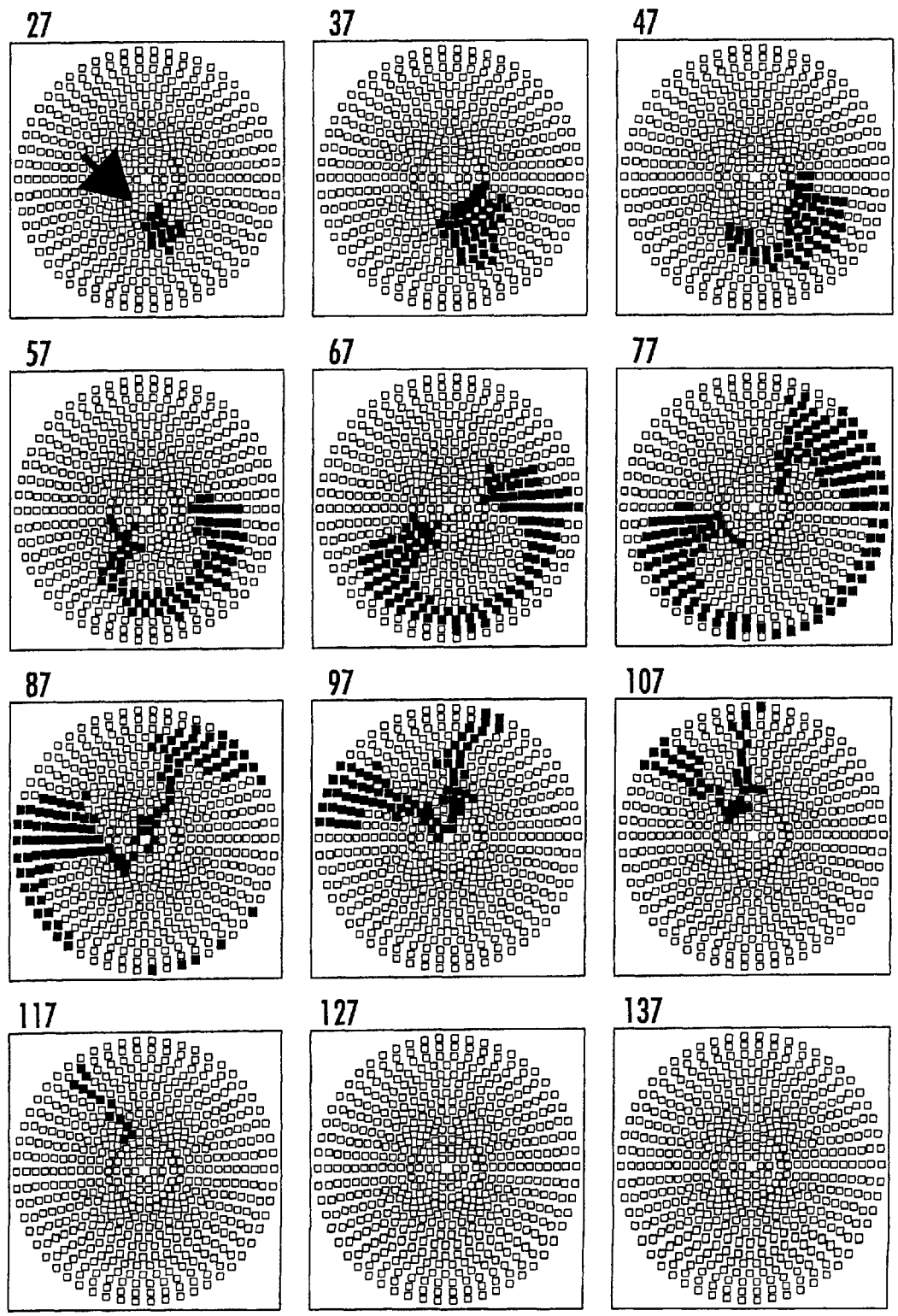

FIG. 7: Examples from one animal of postshock cycle 1 for VFI (Panels A) and NoVFI episodes (Panels B) and of a paced cycle (Panels C). Electrode sites at which dV/dt≦−0.5 V/s at any time during a 10 ms interval are black. Numbers above 20 the frames indicate the start of each interval in ms relative to start of the shock. Sock orientation is shown in FIG. 6D. Arrows indicate the SEA for each cycle. Panel A: Cycle 1 arose at the antero-apical LV, propagated toward the antero-basal LV, and blocked over the RV apex. Panel B: Cycle 1 arose in the same region as in panel A and propagated similarly. Panel C: Activation initiated by pacing from the antero-basal epicardial LV propagated without slowing across the apex. VFI=VF induction, NoVFI=no VF induction, SEA=site of earliest activation, LV=left ventricle, RV=right ventricle.

Figure 7C:
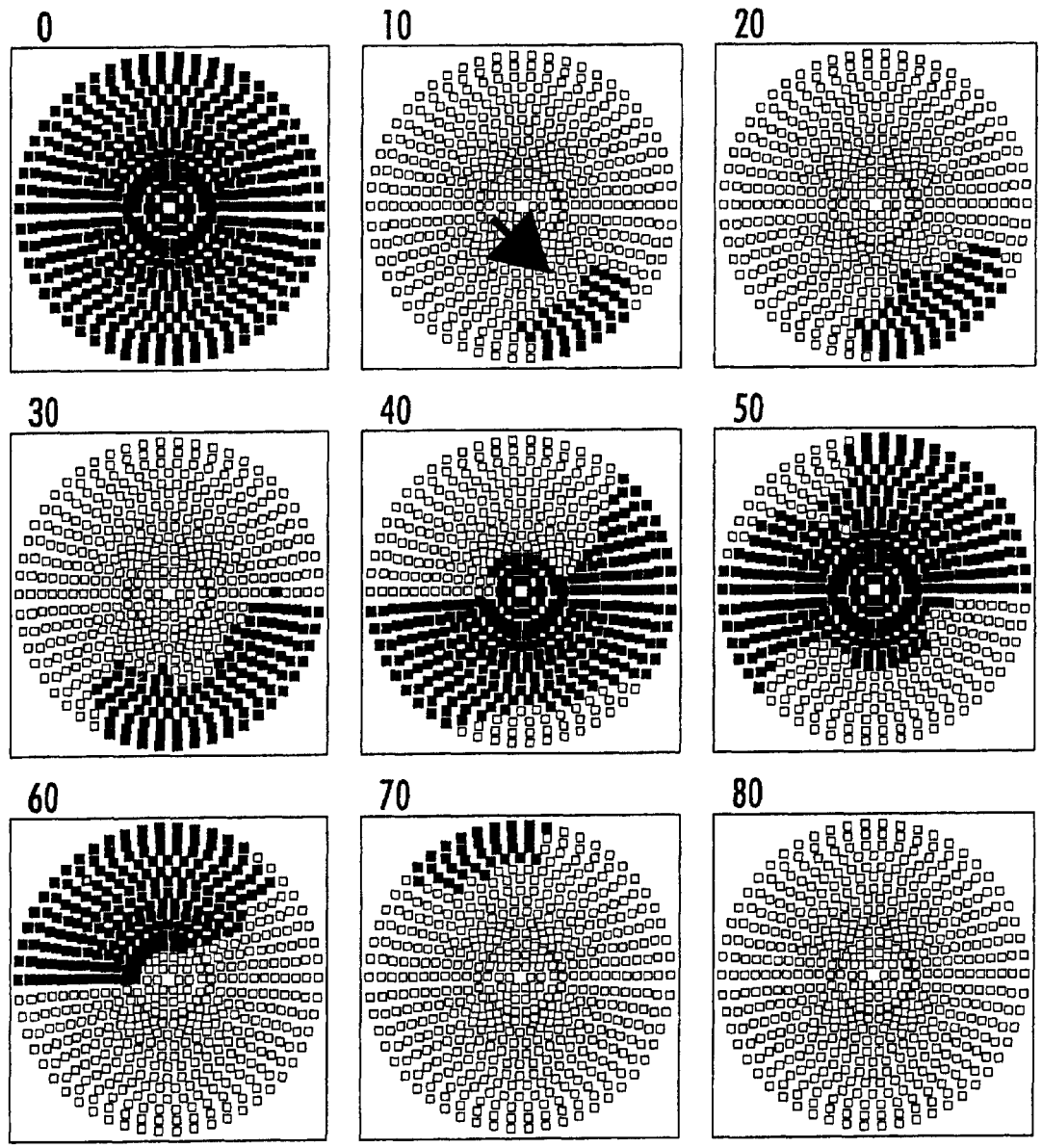
Figure 8:
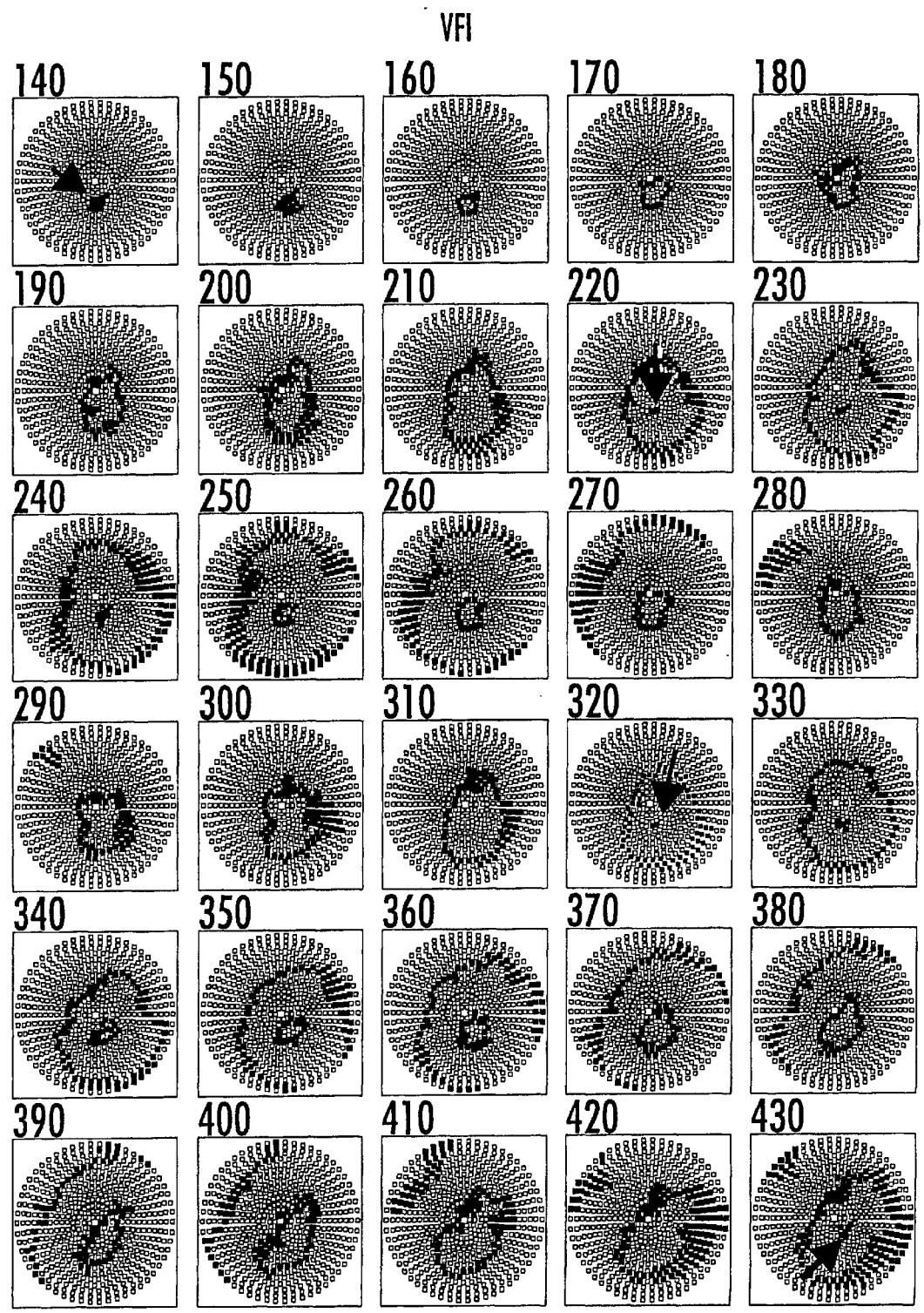
Figure 9A:
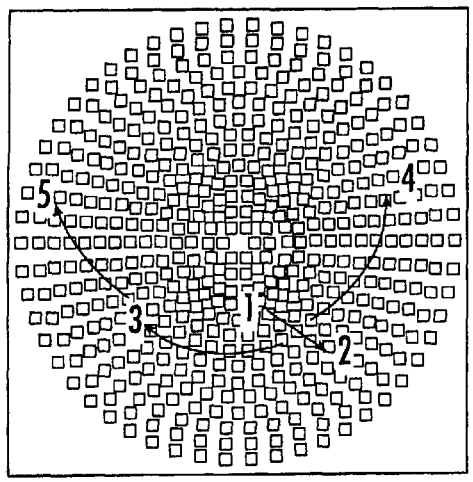
Figure 9B:
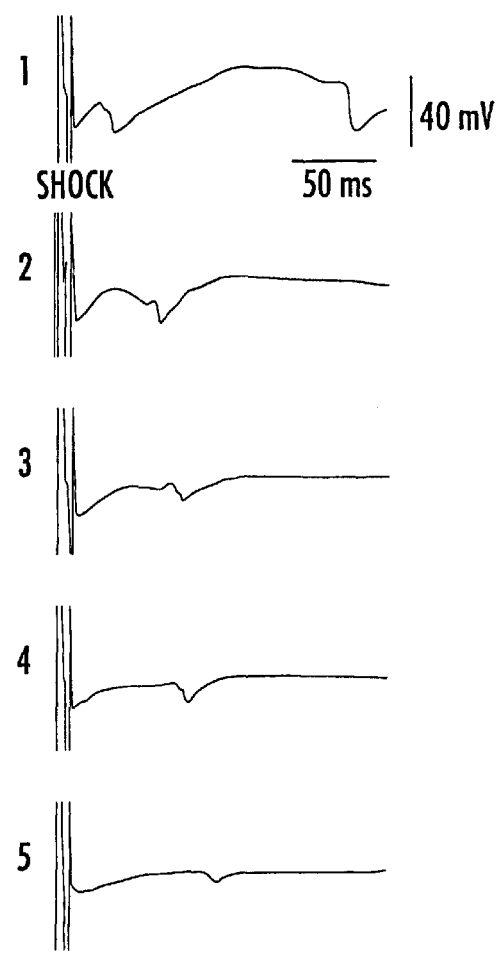
Figure 9C:
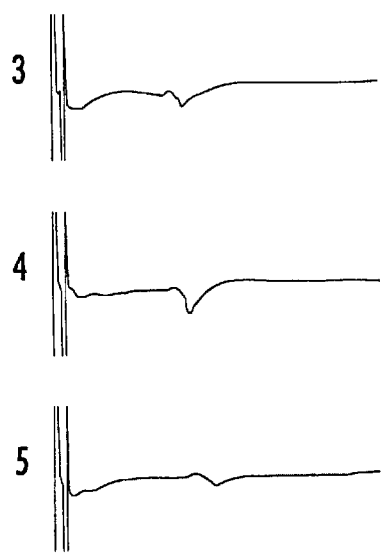
Figure 9D:
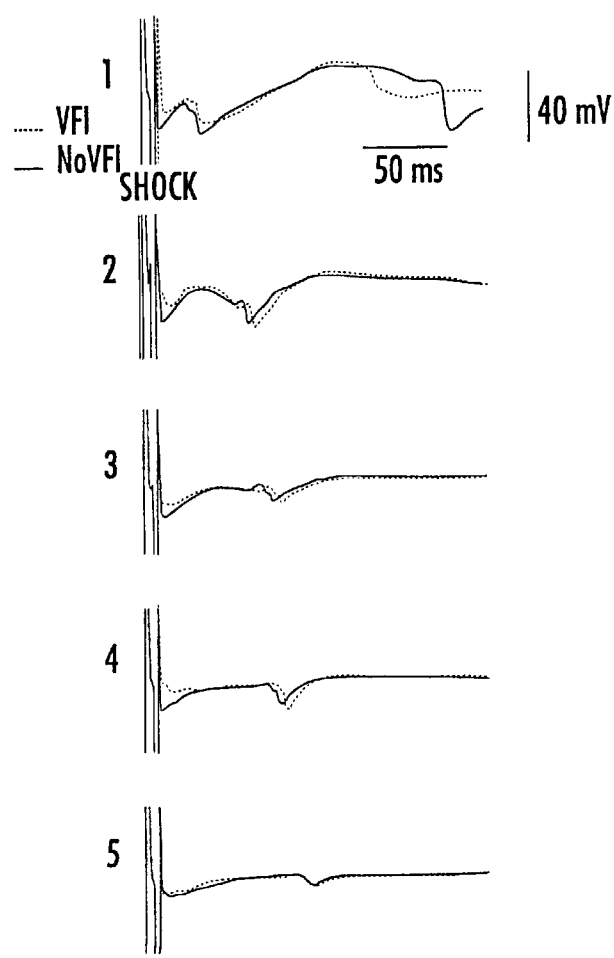

FIG. 8: Postshock cycles 2 to 5 for the same VFI episode (Panel A) and cycles 2 to 4 for the same NoVFI episode (Panel B) shown in FIG. 7. Panel A: The SEA of VFI cycle 2 (140 ms) was in the REA of cycle 1 and activation propagated away in a focal pattern. The third (229 ms), fourth (320.5 ms), and fifth (434 ms) VFI cycles arose before activation from the previous cycle disappeared. Panel B1: NoVFI cycle 2 appeared at 169 ms and propagated in a focal pattern. Panel B2: NoVFI cycle 3 arose at 826 ms on the postero-basal RV and propagated across the entire epicardium faster than cycle 2. Panel B3: NoVFI cycle 4 arose 1444 ms after the shock and was a sinus cycle.

FIG. 9: Selected electrograms from the episodes shown in FIG. 7. Panel A: A polar map with numbers 1 through 5 representing sites where the 5 electrograms shown in Panels B-D were recorded. Arrows represent the direction of propagation of activation. Panel B: Electrograms from the NoVFI episode. Multiple vertical lines are shock artifact. Activation was earliest in electrogram 1 and latest in electrogram 5. The second deflection in electrogram 1 was an activation in cycle 2. Panel C: Electrograms from the VFI episode. The second deflection in electrogram 1 was an activation during cycle 2. Panel D: Electrograms from Panel B (dotted) and Panel C (solid) superimposed.

Figure 10A:
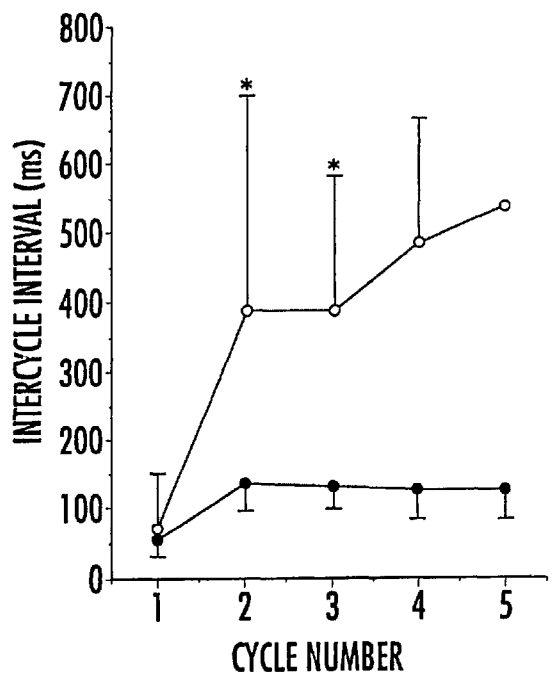
Figure 10B:
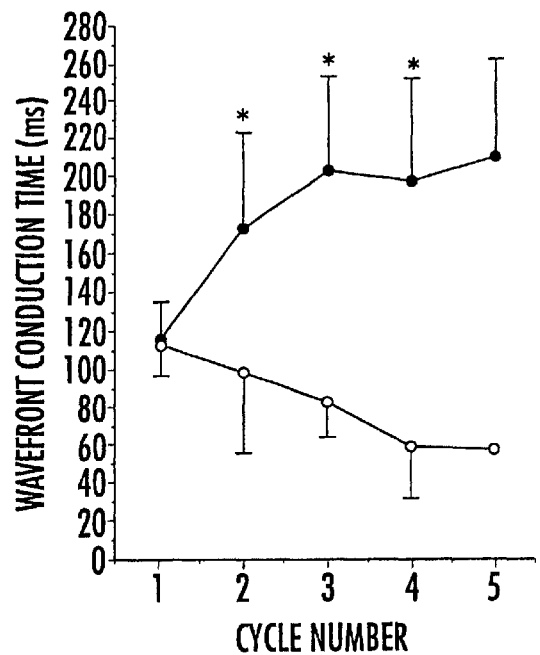
Figure 10:
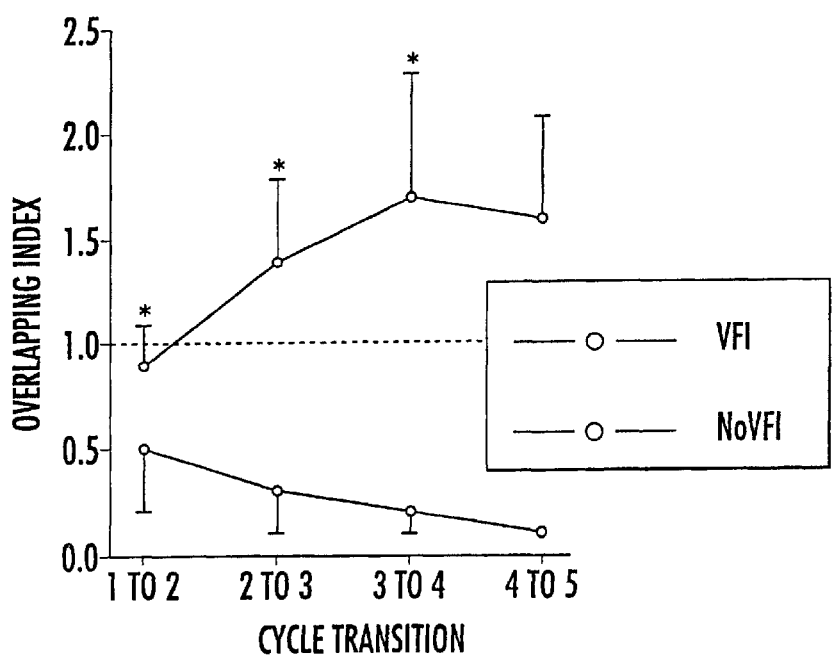

FIG. 10: ICIs (Panel A), WCTs (Panel B), and overlapping index (Panel C) of the first 5 postshock cycles. Only one cycle 5 occurred in the NoVFI episodes, therefore, there is no standard deviation for this cycle and no comparison was made with VFI episodes. *=P<0.05 vs. VFI for a given cycle.

FIG. 11: Examples from the same animal of the first 2 cycles in VFI (Panel A), NoVFI with short ICI (Panel B), and NoVFI with long ICI (Panel C) episodes. Panels A1, B1, & C1: Cycle 1. The SEAs (arrows) were all in the same region and started 45 ms, 48 ms, and 49 ms after the shock, respectively. Activation patterns are all similar. WCTs in Panels A1, B1, and C1 were 122 ms, 120 ms, and 116 ms, respectively. Panel A2, B2, & C2: Cycle 2. The ICI in Panel C2 was longer (454 ms) than in Panels A2 (132 ms) and B2 (146 ms), whereas the WCT in Panel C2 (77 ms) was shorter than in Panels A2 (154.5 ms) and B2 (118 ms). The SEA in Panels A2 & B2, but not C2, were in the same region as cycle 1. An overlapping cycle was present only for the VFI episode (Panel A2, cycle 3 begins at 297 ms).

FIG. 12: Selected electrograms from the VFI (Panel A), NoVFI with short ICI (Panel B), and NoVFI with long ICI (Panel C) episodes shown in FIG. 11. All electrograms were taken from the same site, began 10 ms after the shock, and were 600 ms in duration.

DETAILED DESCRIPTION OF PREFERRED EMBODIMENTS

The present invention is explained in greater detail below. This explanation is not intended to be a detailed catalog of all alternatives for the various elements of the invention, but is instead intended to be illustrative of the invention to those skilled in the art.

"Cycle" herein refers to a wave of activation propagating across the epicardium of the heart, which in the normal, healthy heart is associated with a single contraction of the atria and ventricles, or a single "beat" of the heart.

"Overlapping cycles" as used herein refers to the presence of activation from two cycles on the epicardium of the heart simultaneously.

"Wavefront conduction time" (WCT) as used herein refers to the time interval between the earliest and latest recorded activation for a particular cardiac activation cycle.

"Intercycle interval" (ICI) for cycle [n+1] refers to the time interval between the earliest activation for cycle [n] and the earliest activation for cycle[n+1].

"Overlapping cycle index" (OCI) or "overlapping index" as used herein refers to the ratio: WCT of cycle[n]/ICI of cycle[n+1]. There is no overlapping cycle during cycles when the index is ≦1.

The present invention may be used in conjunction with the treatment of all types of cardiac tachyarrhythmias, including both atrial arrhythmia and ventricular arrhythmia, particularly including atrial and ventricular fibrillation, with defibrillation (including cardioversion) shocks or pulses. The treatment of polymorphic ventricular tachycardia, monomorphic ventricular tachycardia, ventricular fibrillation, and atrial fibrillation are particularly preferred.

Any suitable waveform can be used to carry out the first (or second) arrhythmia therapy pulse or shock, including both monophasic and biphasic waveforms, pacing pulses, series of shocks delivered along the same or different current paths, etc. Amplitude, polarity, and duration of waveforms are not critical and numerous variations will be apparent to those skilled in the art. In general, pacing pulses are 0.5 to 5 milliseconds in duration and 1 to 10, preferably 5, volts in magnitude. Defibrillation pulses are, in general, 2 or 3 to 5 or 10 milliseconds in duration (for a monophasic shock; twice that for a both phases of a biphasic shock) and 200 or 400 to 600 or 900 volts (leading edge amplitude) in magnitude.

The present invention is intended primarily for use on human subjects, but may optionally be carried out on other mammalian subjects for veterinary purposes.

Figure 1:
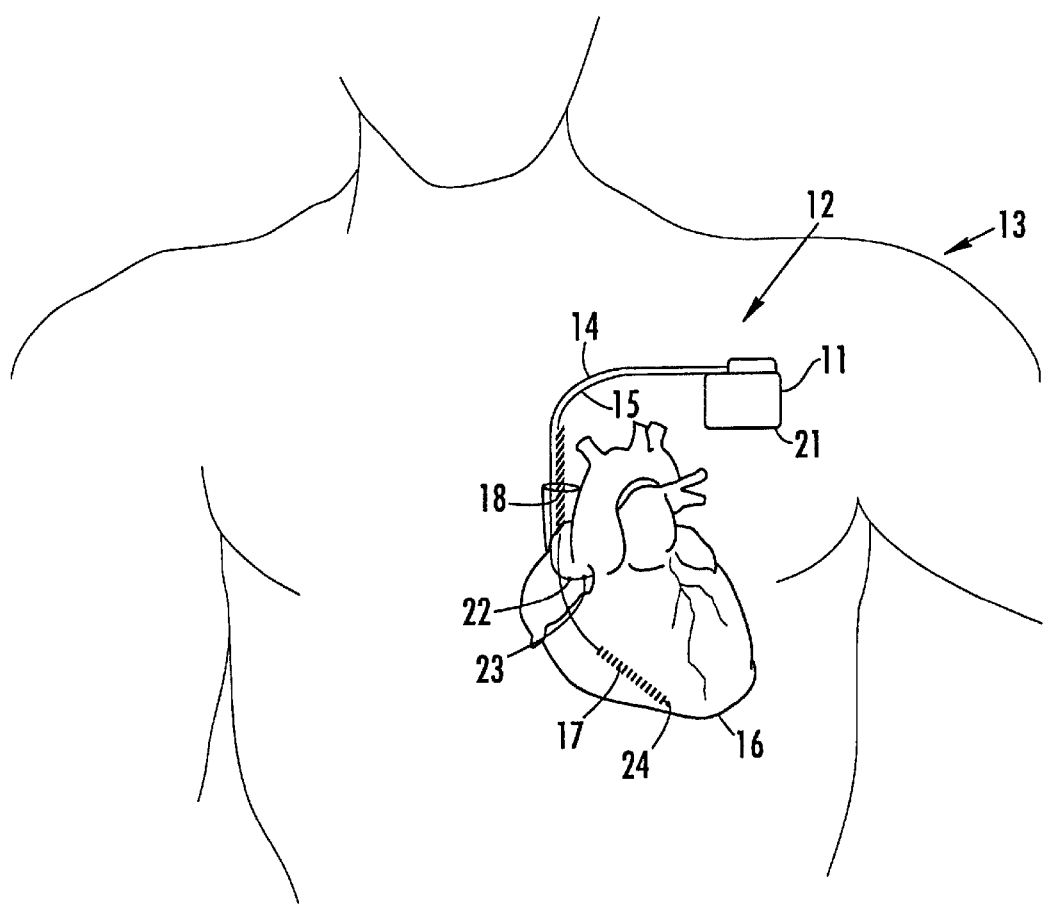
FIG. 1: Illustrates an implantable cardioverter defibrillator (ICD) of the invention implanted in a human subject.

An implantable cardioverter defibrillator (ICD) implementing the present invention is illustrated in FIG. 1. The ICD includes a housing 11 implanted in the pectoral region 12 of a human subject 13 with leads 14, 15 extending into the heart 16. The housing and leads may be implanted in accordance with standard techniques.

The leads carry a pair of defibrillation electrodes 17, 18, with one positioned in the superior vena cava (SVC) and/or right atrium, and another positioned in the apex of the right ventricle (RV). The housing may also include an electrode 21 on the outer surface thereof, typically referred to as a "can" electrode. First and second sensing electrodes 22, 23 are positioned in the right atrium, and an additional sensing electrode 24 is placed on the distal tip of the lead positioned in the right ventricle. The defibrillation electrode in the right ventricle can also serve as a sensing electrode in conjunction with the distal tip electrode. The housing contains a shock circuit comprising a battery and an associated capacitor, and control circuitry associated with each for charging the capacitor from the battery and discharging an appropriate shock through the defibrillation electrodes at the appropriate time. The housing additionally contains amplifiers (see FIG. 4) associated with the sensing electrodes (including defibrillation electrodes that are additionally used as sensing electrodes) for amplifying signals from the heart. All can be implemented in any of a variety of manners known to those skilled in the art. See, e.g., U.S. Pat. No. 5,978,705 to KenKnight et al.; U.S. Pat. No. 5,978,704 to Ideker et al; and U.S. Pat. No. 5,987,354 to Cooper et al. (the disclosures of all United States patent references cited herein are to be incorporated by reference herein in their entirety. The amplifiers are associated with a determining means such as a microprocessor or controller that senses events and triggers appropriate therapy through the a charging and/or triggering signal to the control circuitry described above. Determination of overlapping cycles can be determined by any suitable device, including hardware such as a microprocessor, a software device, combinations of hardware and software, etc., one embodiment of which is illustrated in FIGS. 4–5 below.

Figure 2:
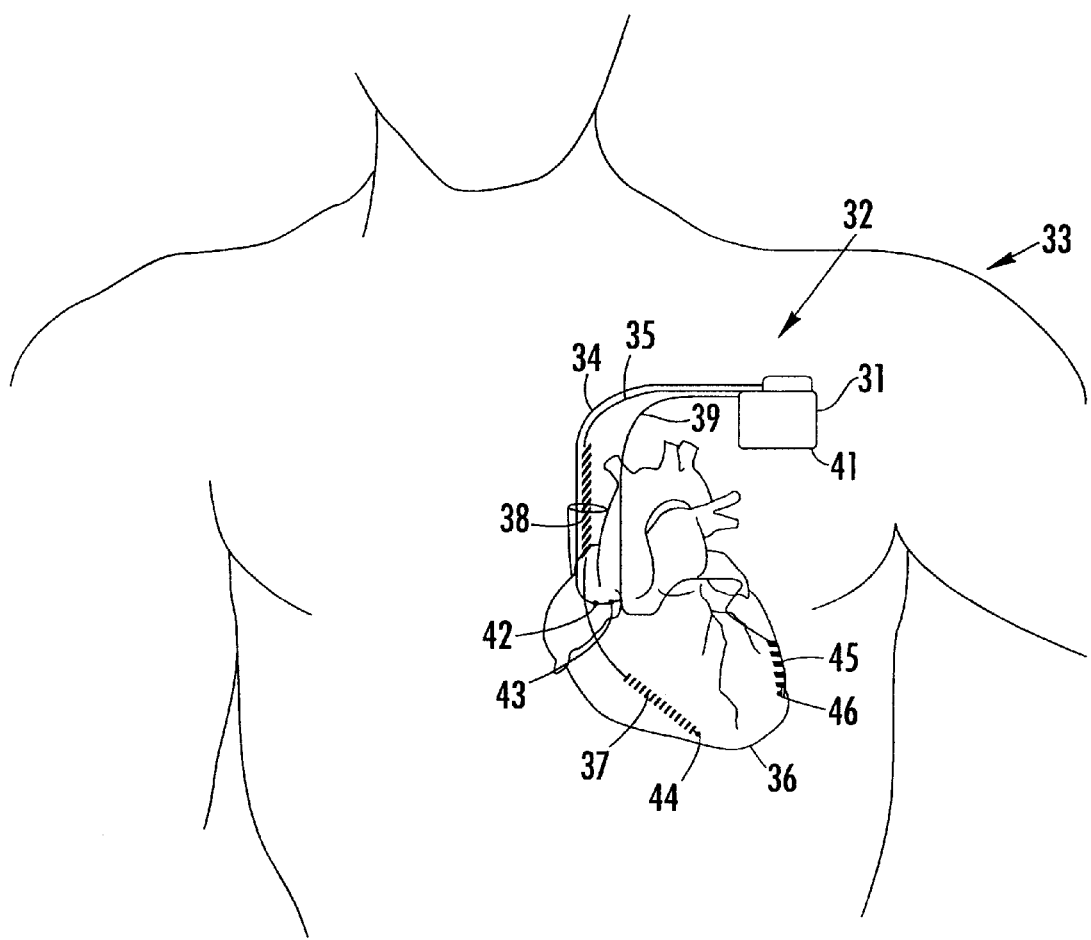
FIG. 2: Illustrates another ICD of the invention implanted in a human subject.

An alternate embodiment of an ICD incorporating the present invention is illustrated in FIG. 2. The ICD again includes a housing 31 implanted in the pectoral region 32 of a human with three leads 34, 35, 39 extending into the heart. The first two leads are positioned in like manner as in FIG. 1; the third lead is positioned through the ostium of the coronary sinus and into a vein on the surface of the left ventricle, typically a tributary of the coronary vein. The housing and leads may be implanted in accordance with standard techniques. One of the defibrillation electrodes is positioned in the superior vena cava and/or right atrium, another is positioned in the right ventricle, and the other 45 is positioned on the surface of the left ventricle. The housing may also include a can electrode 41 on the outer surface thereof. First and second sensing electrodes 42 43 are positioned in the right atrium, and an additional sensing electrode 44 is placed on the distal tip of the lead positioned in the right ventricle. The defibrillation electrode in the right ventricle can also serve as a sensing electrode in conjunction with the distal tip electrode. A pace/sense electrode 46 is positioned on the distal tip of the left ventricle lead, for delivering pacing pulses or sensing electrical events. The housing contains a shock circuit comprising a battery and an associated capacitor, and control circuitry associated with each for charging the capacitor from the battery and discharging an appropriate shock through the defibrillation electrodes at the appropriate time. The housing additionally contains amplifiers associated with the sensing electrodes (including defibrillation electrodes that are additionally used as sensing electrodes) for amplifying signals from the heart. All can be implemented in any of a variety of manners known to those skilled in the art, as described above. The amplifiers are associated with a microprocessor or controller that senses events and triggers appropriate therapy through the a charging and/or triggering signal to the control circuitry described above, as illustrated in FIGS. 4–5 below.

Figure 3:
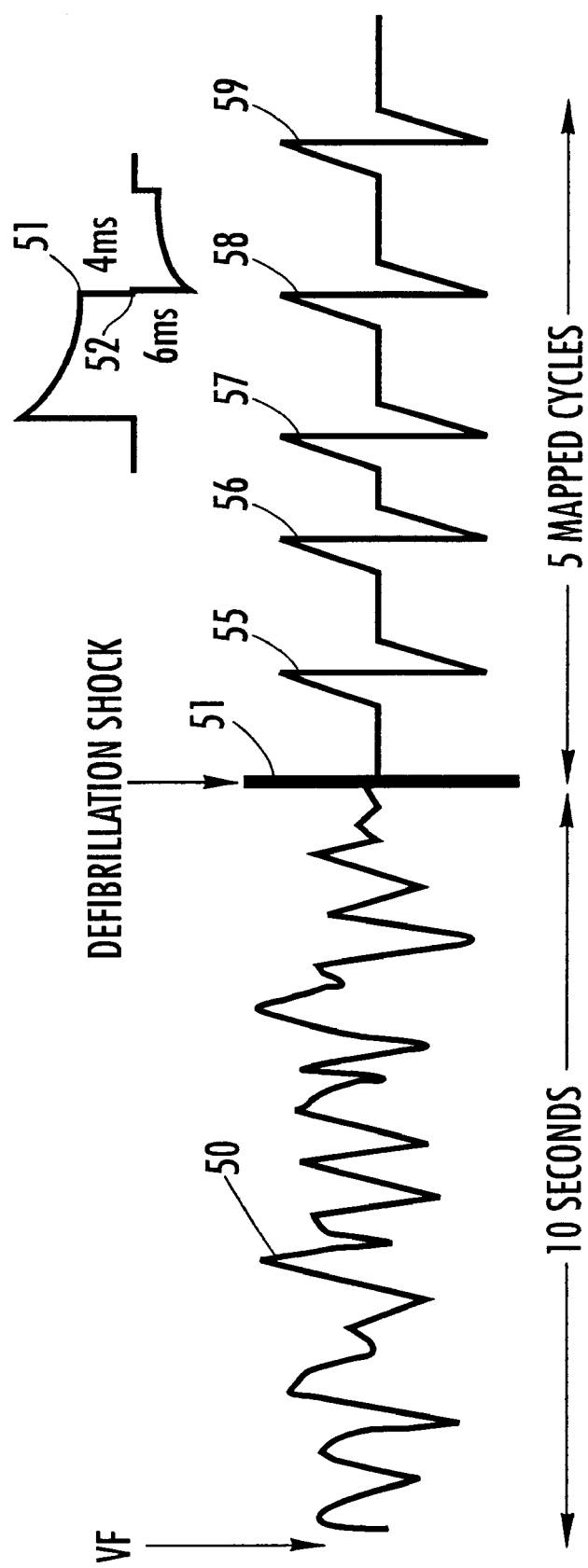
FIG. 3: Schematically illustrates a defibrillation protocol of the invention, following experimental ventricular fibrillation (VF) induction, the delivery of a defibrillation shock (biphasic, 6 milliseconds in duration for the first phase and 4 milliseconds in duration for the second phase), and the monitoring of the first five postshock cardiac cycles.

FIG. 3 schematically illustrates one defibrillation protocol that may be used in implementing the present invention, as may be carried out with defibrillation electrodes positioned in the SVC and RV apex. After detection of a period of ventricular fibrillation (VF) 50 a defibrillation shock 51 is given. The defibrillation shock, as illustrated, is a biphasic, exponential waveform shock, 6 milliseconds in duration for the first phase and 4 milliseconds in duration for the second phase, with an interphase delay 52 of 0.2 milliseconds. Five cardiac cycles 55, 56, 57, 58, 59, 60 after the defibrillation shock are monitored to detect the presence of absence of overlapping cycles and determine the need for a further defibrillation shock.

Figure 4A:
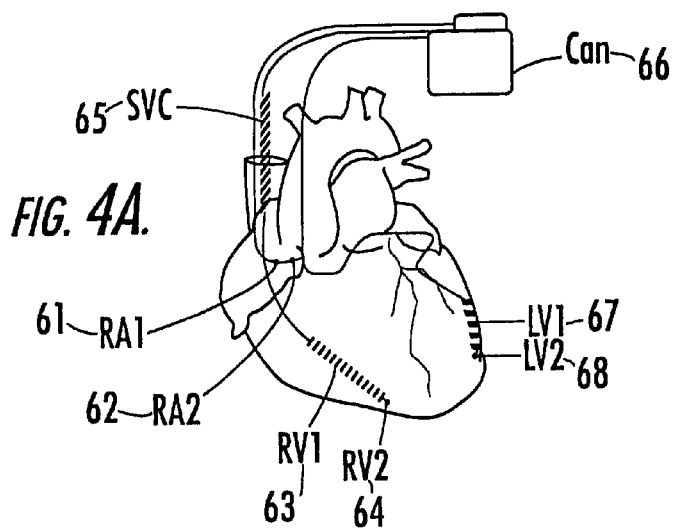
FIG. 4: Schematically illustrates a system and method for carrying out the present invention with an ICD similar to that of FIG. 2.

FIGS. 4a–e schematically illustrates the detection of electrical events that may be indicative of the need for shock, as they would be implemented in a device of FIG. 4a. Pairs or sets of electrodes (right atrium 1 and right atrium 2; RA1 and RA2; 61, 62) (right ventricle 1 and right ventricle 2; RV1 and RV2; 63, 64) (right ventricle 1 and superior vena cava plus Can; RV1 and SVC+Can; 63, 65, 66) (left ventricle 1 and left ventricle 2; LV1 and LV2; 67, 68) are each associated with a differential amplifier 70, 71, 72, 73, each of which is in turn connected to a bandpass filter 76, 77, 78, 79, which is in turn associated with a sensed event detector. The sensed event detectors may be included in or connected to a microprocessor controller 80 for determining whether to deliver a shock or therapeutic pulse by a trigger signal through line 81 to a control circuit (not shown) such as described in conjunction with FIG. 1 or 2 above.

Figure 4C:
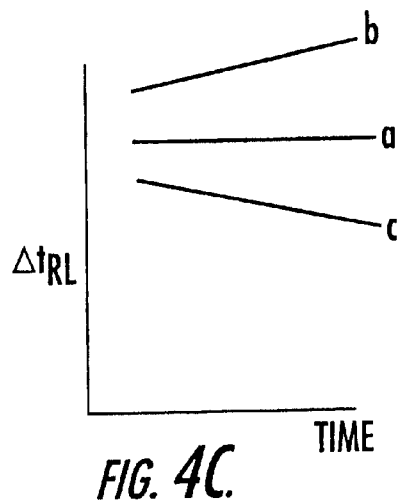
Figure 5:
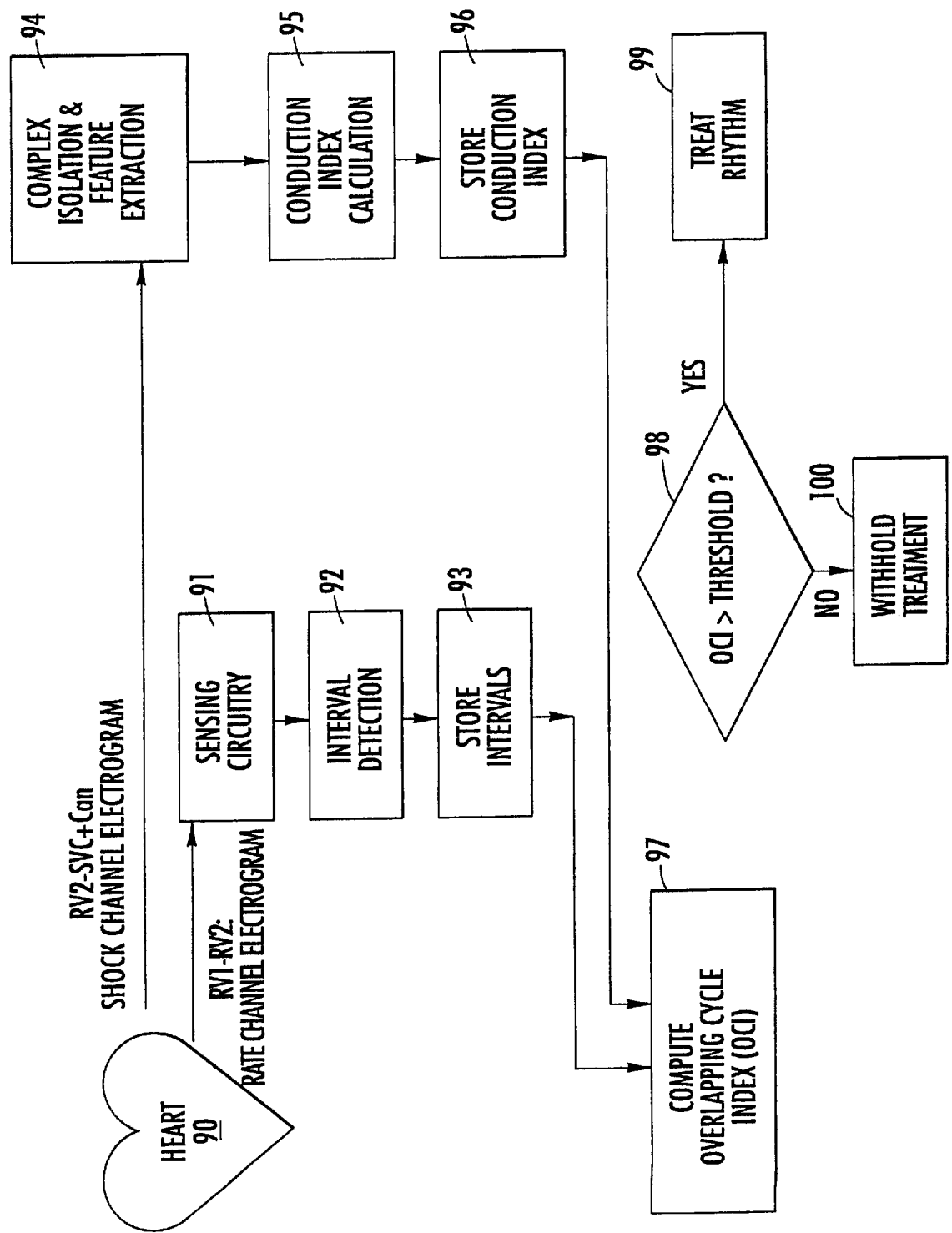
FIG. 5: Schematically illustrates one logic circuitry or program that may be used to carry out the present invention.

By differentially amplifying and filtering signals from two spaced apart electrodes, sensed events can be generated by the sensed event detector circuitry, which then can be compared with other events sensed elsewhere in the heart. The first column immediately to the right of the sensed event detectors represents events sensed in normal sinus rhythm (NSR), with the difference in time from the right atrium to the right ventricle ($\Delta t_{AV}$), being determined as shown, and by comparing sensed events in the right ventricle to the left ventricle, the difference in time from the right ventricle to the left ventricle ($\Delta t_{LR}$ or $\Delta t_{RL}$) being determined as shown. As shown in the graph of FIG. 4c, the $\Delta t_{RL}$ will differ over time during ventricular tachycardia (VT) that is sustained and monomorphic (trace "a"), VT with a high probability of degenerating into ventricular fibrillation (VF) (trace "b"), and VT that is likely to spontaneously terminate (trace "c").

Figure 4D:
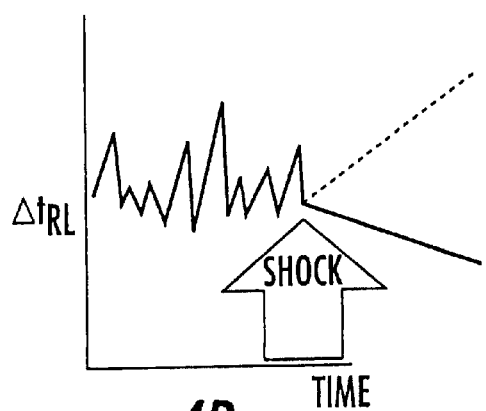

FIG. 4d illustrates the $\Delta t_{RL}$ trend during the VF shown in the third column of FIG. 4e. As illustrated $\Delta t_{RL}$ during VF tends to fluctuate over time as a consequence of the discoordinated activation in the ventricles. This discoordination may be sensed by the microprocessor or control circuitry 80 over time and used to trigger a shock. After the shock is applied (arrow in FIG. 4d), the $\Delta t_{RL}$ increases over time for shocks that failed to terminate arrhythmia (dotted line), and decreases over time for shocks that successfully terminated the arrhythmia (solid line).

Overlapping cycles can be conveniently measured in an apparatus as described herein by the procedure set forth in FIG. 5. Sensing circuitry 91 associated with RV1 and RV2 electrodes in a heart 90 can provide a rate channel electrogram for interval detection 92 and interval storage 93. The RV2 electrode, SVC electrode and can electrode can provide information for the isolation and extraction of complex features 94, from which a conduction index 95 can be calculated and stored 96. The overlapping cycle index (OCI) can then be computed 97 after a therapeutic pulse from the stored intervals and the stored conduction index. If the OCI exceeds a preset threshold in a comparison step (e.g., is greater than 1), then a therapeutic pulse may be administered 99 through a trigger signal from the control circuitry to discharge the storage capacitor; if the OCI does not exceed a preset threshold, then no therapeutic pulse is given 100.

Additional features can also be added to the invention without affecting the function of the invention and result thereof. Such additional features include, but are not limited to, safety features such as noise suppression or multiple wave monitoring devices (R and T), verification checking to reduce false positive, precardioversion warning, programmed delayed intervention, bipolar configured sensing electrodes, intermittently activated fibrillation detector to reduce energy drain, a switching unit to minimize lines from the pulse generator (to name a few).

Although the system is described herein primarily as an implantable system, it will be appreciated by those of ordinary skill in the art that the invention could also be incorporated into an external system which employs catheters to position the electrodes for a short time within a patient's heart.

The present invention is illustrated further in the Examples set forth below.

EXAMPLES

Influence of Postshock Epicardial Activation Patterns on the Initiation of Ventricular Fibrillation By Upper Limit of Vulnerability Shocks A strong stimulus during the vulnerable period can induce repetitive responses that either halt without inducing ventricular fibrillation (VF) or degenerate into VF (Wiggers C J, Wégria R., Am J Physiol. 1940;128:500–505). Most proposed mechanisms of VF induction based on this finding, such as the non-uniform dispersion of refractoriness hypothesis (Han J, Moe G K. Nonuniform recovery of excitability in ventricular muscle. Circ Res. 1964;14:44–60), imply that activation immediately after the shock in a successful VF induction (VFI) differs from that in a failed VF induction (NoVFI) (Shibata N et al., Am J Physiol. 1988;255: H891–H901; Chen P-S. et al., Circ Res. 1988;62:1191–1209).

Previous studies using a range of shock strengths and timings showed that the interval between the shock and the first global postshock activation is shorter for VFI than for NoVFI shocks (Shibata N et al., Am J Physiol. 1988;255: H891–H901; Chen P-S et al., J Clin Invest. 1986;77:810–823). However, comparison of VFI and NoVFI episodes following shocks of the same strength has not been reported.

In this study, we determined activation patterns following shocks of identical strength and timing. A shock strength near the upper limit of vulnerability that induced VF in approximately 50% of the trials ($ULV_{50}$) was used. We tested the hypothesis that the activation pattern immediately after VFI shocks differed from that after NoVFI shocks.

I. Materials and Methods

Animal Preparation.

Six pigs (30–35 kg) of either sex were anesthetized, monitored, and maintained under physiologic conditions as described previously (ChattipakornN et al., Circulation. 1998;97:1401–1410). The chest was opened through a median sternotomy, and the heart was suspended in a pericardial cradle.

Two catheter-mounted platinum-coated titanium coil electrodes delivered S2 shocks (CPI-Guidant Corp). A 34-mm electrode was inserted into the right ventricular (RV) apex (FIG. 6A) and was cathode for the first phase of the S2 shock. A 68-mm electrode was positioned at the junction of the superior vena cava (SVC) and right atrium. An electrode at the catheter tip was used for S1 pacing. Unipolar pacing electrodes were sutured to the RV outflow tract and anterobasal LV free wall.

Figure 6B:
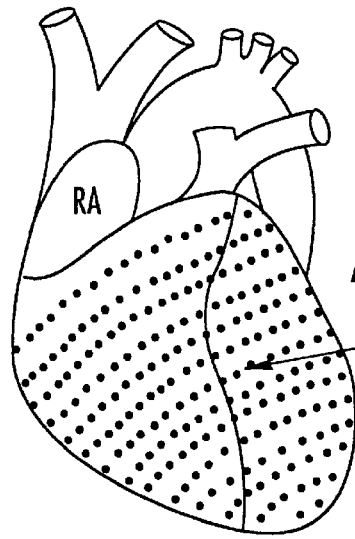

The elastic sock had 14 rows of electrodes (Chattipakorn, N et al., supra) and was pulled over the ventricles to record unipolar epicardial electrograms (FIG. 6B). Each Ag/AgCl electrode was 1 mm in diameter and approximately 4 mm from its neighbors. Two 3-mm diameter Ag/AgCl disc electrodes were sutured to the aortic root 5 mm apart, to serve as reference for the unipolar recordings and ground for the mapping system.

Electrograms were bandpass filtered between 0.5 and 500 Hz and recorded at 2 kHz with 14 bit precision (Smith W M et al., In: Shenasa M, Borggrefe M,Breithardt G, eds. Cardiac Mapping. Mount Kisco, N.Y.: Futura Publishing Company, Inc.: 1993:251–260). Five ms before each shock, amplifier coupling was changed from AC to DC, and amplifier gains were decreased. Approximately 9 ms after the shock, initial conditions were restored.

Experimental Protocol.

Figure 6C:
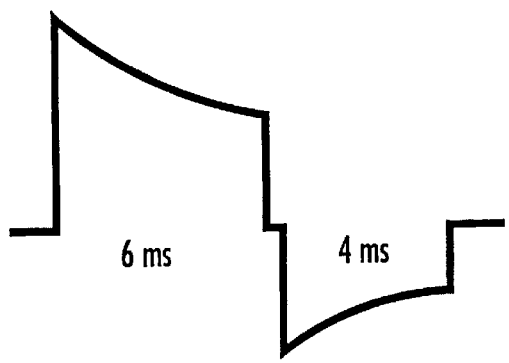

Initially, normal sinus rhythm and pacing from each pacing electrode were recorded to orient the mapping array. The intrinsic R-R interval and diastolic pacing threshold (DPT) were measured. S1 stimuli were constant current, unipolar, 5-ms, monophasic pulses. S2 shocks were biphasic truncated exponential single capacitor waveforms (FIG. 6C) (Ventritex corp., HVS-02). Delivered voltage and current were displayed and total delivered energy was calculated by a waveform analyzer (DATA 6100, Analogic Inc.).

Ten S1 stimuli were delivered 3 times, and the average coupling interval (CI) between the last S1 and the beginning, peak, and end of the T-wave in limb leads 1 or II were determined (Huang J et al., Circulation. 1997;96:1351–1359). These intervals were recalculated every 5 VF episodes.

ULV Determination.

Ten S1 stimuli at 5–10 times cathodal DPT were delivered at an interval of 300 ms or 80% of the intrinsic R—R interval, whichever was shorter. S2 leading edge voltage was initially 500V. The first S2 was delivered at the peak of the T-wave. Subsequent S1–S2 CIs scanned the T-wave in 10 ms steps. For example, if the initial CI was 200 ms, then subsequent CIs were 210, 190, 220, 180 ms, etc.

ULV shock strength was determined using a modified up-down protocol with 40V and 20V steps as described by Huang et al., supra. Successive shocks were separated by 15 sec. The lowest shock strength that did not induce VF at any C1 was defined as the ULV. Next, the T wave was scanned with a shock 10V below the ULV (sULV) in 10 ms steps starting at the last S1–S2 C1 that induced VF during the ULV determination. The T-wave was scanned alternately increasing and decreasing the S1-S2 interval until all Cis inducing VF were determined. The mean C1 at which VF was induced with sULV shocks was used as the S1-sULV CI (sCI).

Mapping of VF Induction.

Activations before and after 10 shocks of sULV strength delivered at the sCI were mapped. Ten sec after a shock induced VF, a 20–30 J rescue shock was delivered. If the percent of VFI was not 40–60%, sULV strength was increased or decreased in 10-V steps and a new sCI was determined. Then, 10 shocks at the new sULV strength were delivered at the new sCI. This protocol was repeated until the incidence of VFI episodes was 40–60%, indicating S2 shock strength was ~$ULV_{50}$. Only this last group of 10 shocks were analyzed. VF episodes were at least 4 min apart. At the end of the study, the animal was euthanized by VF.

Data Analysis.

Activations were analyzed by animating the first derivative (dV/dt) of the unipolar electrograms on a polar projection of the ventricular epicardium (FIG. 6D) on a computer (Chattipakorn, N et al., supra). The dV/dt was computed using a 5-point digital filter and activation was identified when $dV/dt \leq -0.5$ V/s.

The preshock interval was defined as the time from the beginning of the last paced cycle to the beginning of the shock. The first 5 activation cycles following the shocks were analyzed. In NoVFI episodes, only ectopic cycles were analyzed, so less than 5 activations were sometimes examined. The site of earliest activation (SEA) of each cycle was defined as the location of the first electrode that detected activation. The intercycle interval (ICI) for cycle[n+1] was the interval between earliest activation for cycle[n] and earliest activation for cycle[n+1]. The ICI for cycle 1 was the postshock interval. Wavefront conduction time (WCT) was the time between activation at the SEA and at the site of latest activation of each cycle. Overlapping cycles, i.e. activation from 2 cycles on the epicardium simultaneously, were detected by dividing the WCT of cycle[n] by the ICI of cycle[n+1] (the overlapping index). Overlapping cycles were absent when the index was $\leq 1$.

To compare the first postshock cycles (or the last paced cycles) of 2 shock episodes, we computed a similarity cross-correlation function,(Stearns S D, David R A. *Signal Processing Algorithms in Fortran and C*. Englewood Cliffs, N.J.: Prentice Hall Press; 1993) $s_{ij}$, where i and j identify the 2 episodes.

$$c_{ij}(\tau) = \sum_{n=1}^{504} \sum_{t=\max(1-\tau,1)}^{\min(T_i,T_j-1)} P_i(n,t) P_j(n,t+\tau) - (T_i - 1) \leq \tau \leq \tau T_j - 1 \quad (1)$$

$P_i$ and $P_j$ are matrices containing the unipolar potentials during the 2 cycles. Each row (n) represents a recording electrode and each column (t) a time sample. Comparison began 20 ms after the shock (or 5 ms after the last S1 pacing for the last paced cycles) and ended when activation from the cycle was no longer recorded. Respective durations of the 2 cycles are $T_i$ and $T_j$, n is the electrode number, and T is a temporal lag. We found the maximum of this function, $c_{ij} = \max[c_{ij}(\tau)]$ and the lag, $\tau_m$ at which it occurred. $s_{ij}$ was evaluated by normalizing $c_{ij}$:

$$s_{ij} = \frac{c_{ij}}{\sqrt{\sum_{n=1}^{504} \sum_{t=\max(1-\tau_m,1)}^{\min(T_i,T_j-1)} P_i(n,t)^2 \sum_{n=1}^{504} \sum_{t=\max(1-\tau_m,1)}^{\min(T_i,T_j-1)} P_j(n,t+\tau_m)^2}} \quad (2)$$

Although this method does not provide specific information about the activation sequence, it is a sensitive indicator of the similarity between 2 different cycles ($s_{ij}=1$ indicating an exact match) and of any temporal shift between the 2 cycles (indicated by a nonzero lag, $\tau_m$). The similarity function and lag were computed for all 45 possible pairs of first postshock cycles in each animal.

The SEA of the first postshock cycle was determined from the animations of activation. SEAs of different shock episodes from an animal were considered to be in the same region of earliest activation (REA) if they were at the same site or at the nearest neighbors of the site. For each animal, the percent of first cycle SEAs in the REA with the most SEAs and the percent of subsequent cycle SEAs in this first cycle REA were determined. This parameter is called SEA repeatability for each cycle.

Statistical Analysis.

VFI and NoVFI episodes was compared with the Student's t-test for paired and unpaired data. Similarity of the first postshock cycle and of the last paced cycle from different shock episodes and of the dV/dt at the SEA of the postshock cycles were compared using one-way Analysis of Variance. When statistical significance was found, individual comparisons were performed with Fisher's post-hoc test. Values are shown as mean±standard deviation (SD). Differences were considered significant for $P \leq 0.05$.

II. Results

Thirty of the 60 shocks in the 6 pigs were VFI episodes. One VFI episode was excluded because the last S1 stimulus did not capture. The sULV shock voltage was 498±112 V. The sCI was 214±14 ms. To determine $ULV_{50}$, 15±11 shocks were required. DPT was 0.2±0.1 mA. Heart weight was 154±45 gms. For each animal, delivered shock voltage for the 10 shocks was nearly constant (%SD of 0.1–0.3). Repeatability of the shock potential distribution at the 504 electrodes was measured in 1 pig. The mean correlation coefficient of the potentials was 0.99535 0.004 for all 10 shocks.

The preshock interval and WCT of the last paced cycle before the shock was not different between VFI and NoVFI episodes (Table 1). The similarity of the last paced cycle before the shock (Table 2) was not different suggesting that the activation sequence of the last paced cycle was constant for all 10 shock episodes.

TABLE 1

Preshock interval and wavefront conduction time (WCT) of the last paced cycle

|  | VFI | No VFI |
| --- | --- | --- |
| Preshock interval (ms) | 203 ± 14 | 203 ± 13 |
| WCT (ms) | 60 ± 6 | 59 ± 5 |

VFI = VF induction, No VFI = no VF induction

TABLE 2

Mean correlation and temporal lag of the last paced cycle

|  | Correlation of potential | Temporal lag (ms) |
| --- | --- | --- |
| VFI-VFI | 0.9998 ± 0.0002 | 1 ± 1.5 |
| VFI-No VFI | 0.9998 ± 0.0006 | 1 ± 1.5 |
| No VFI-No VFI | 0.9997 ± 0.0009 | 1 ± 1 |

Cycle 1 SEA. Cycle 1 SEAs were always at the anteroapical LV. While the cycle 1 SEA varied slightly between animals, it was highly repeatable for each animal (Table 3) showing that the first postshock cycle appeared in the same epicardial region regardless of shock outcome.

Maximum dV/dt of activation at the cycle 1 SEA was not different for VFI and NoVFI episodes (Table 3). Mean dV/dt at the SEA of cycles 2 to 5 was less negative than that of cycle 1 for VFI episodes (P<0.01). However, no dV/dt differences were found among the first 5 postshock cycles in NoVFI episodes. For VFI episodes, SEA repeatability for cycles 2–5 (Table 3) was slightly lower than for cycle 1 because the SEA of cycles 2–5 moved a short distance, 2±3 electrodes, away from the cycle 1 REA. However, the SEA of cycles 2–5 in NoVFI episodes moved a much greater distance away from the cycle 1 REA, 9±4 electrodes (P<0.002 vs. VFI episodes).

TABLE 3

Repeatability of site of earliest activation (SEA) and dV/dt

| Postshock Cycle | SEA Repeatability (%) | | dV/dt (V/s) | |
|---|---|---|---|---|
| | VFI | No VFI | VFI | No VFI |
| 1 | 93 ± 10 | 97 ± 8 | −2 6 ± 0.9* | −2.6 ± 0.9 |
| 2 | 60 ± 33 | 50 ± 50 | −1.7 ± 0.9 | −2.8 ± 1.4 |
| 3 | 44 ± 29 | 0 ± 0 | −1.4 ± 0.7 | −2.7 ± 2.0 |
| 4 | 33 ± 29 | 0 ± 0 | −1.8 ± 1.0 | −2.0 ± 0.2 |
| 5 | 16 ± 24 | 0 | −1.3 ± 0.8 | −2.5 |

* = P < 0.01 vs. cycles 2–4 in VFI episodes.

Propagation Pattern in the VFI Episodes.

A typical VFI episode is shown in FIG. 3A (first cycle) and FIG. 8A (subsequent cycles). All 5 cycles began in the antero-apical LV 36, 140, 229, 320.5, and 430 ms after the shock, respectively. Cycle 1 initially propagated toward the LV base, blocking at the RV apex. It continued bilaterally around the apex, rejoining on the posterior RV to complete activation. Subsequent cycles did not block at the RV apex and activated both ventricles in a more radial pattern from apex to base. WCTs increased progressively up to cycle 3, then slightly decreased (89, 161, 215, 170, and 160 ms, respectively). Cycle 2 did not overlap temporally with cycle 1; however, subsequent cycles all overlapped with their immediate predecessor.

Propagation Pattern in the NoVFI Episodes.

Cycle 1 after a NoVFI shock in the same animal (FIG. 7B) was nearly identical to cycle 1 of the VFI episode. This first-cycle similarity is also apparent in the electrograms (FIG. 9). Since cycle 1 for both episodes blocked at the RV apex, we paced from the antero-basal LV in the absence of shocks to establish there were no anatomical or functional barriers at the apex to cause the block (FIG. 7C).

Cycle 2 from this NoVFI episode (FIG. 8-B1) followed a pathway similar to the VFI cycle 2, but began later and conducted faster. Overlapping cycles were absent. Cycles 3 (FIG. 8-B2) and 4 (FIG. 8-B3) arose after long delays from different SEAs and had fast WCTs (73 and 38 ms, respectively). Cycle 4 was sinus and not analyzed.

Postshock ICIs.

The mean ICI (FIG. 10A) of cycle 1 did not differ between VFI (51±23 ms) and NoVFI episodes (n=24, 68±78 ms). The SD of NoVFI episodes was high due to one episode with an extremely long postshock interval (461.5 ms). This episode had its SEA near the postero-basal LV, whereas the SEAs from other episodes in this animal were at the antero-apical LV. If this NoVFI episode is excluded, the mean postshock interval for NoVFI episodes becomes 54±23 ms (P=0.6 vs. VFI). ICIs for VFI episodes were significantly shorter than for NoVFI episodes for cycle 2 (138±38 vs. 387±312 ms) and cycle 3 (132±31 vs. 389±193 ms) (n=12 and 10, respectively). For cycle 4, the mean ICI for VFI (126±40 ms) was shorter than for NoVFI (484±182 ms) episodes; however, the difference was not significant, probably because there were only 5 NoVFI episodes with a fourth ectopic cycle. ICIs of cycle 5 were not compared since only one NoVFI episodes had a cycle 5 (537 ms). ICIs of cycle 5 for VFI episodes were 128±41 ms.

Postshock WCTs.

The WCT (FIG. 10B) of cycle 1 did not differ between VFI (116±19 ms) and NoVFI episodes (113±16 ms). The mean WCTs of cycles 2 (172±51 vs. 99±44 ms), 3 (203±51 vs. 83±18 ms), and 4 (197±55 vs. 59±25 ms) were significantly longer for VFI than for NoVFI episodes (P<0.01). WCT of the single cycle 5 for NoVFI episodes was 58 ms. WCT of cycle 5 for VFI episodes was 210±53 ms.

In all VFI episodes, overlap occurred during cycles 2–3, 3–4, and 4–5 (overlapping index>1) but not cycles 1–2 (overlapping index<1) (FIG. 10C). In contrast, there was no overlap among the first 5 ectopic cycles in any NoVFI episode.

Correlation of 504 Electrograms of Cycle 1.

The similarity function, $s_{ij}$, and temporal lag, $\tau_m$, were compared for all possible combinations of first cycles in each animal and divided into 3 groups: VFI vs. VFI, VFI vs. NoVFI, and NoVFI vs. NoVFI episodes (Table 4). There were no differences in any group for either variable. The very high similarity and short temporal lag among different episodes indicate that first postshock cycles were nearly identical whether or not VF was initiated.

TABLE 4

Mean correlation and temporal lag of postshock first cycles

| | Correlation of potential | Temporal lag (ms) |
|---|---|---|
| VFI-VFI | 0.9987 ± 0.0019 | 1 ± 4 |
| VFI-No VFI | 0.9989 ± 0.0017 | 1 ± 3 |
| No VFI-No VFI | 0.9993 ± 0.0011 | 0.4 ± 2 |

Cycle 2 in NoVFI Episodes.

In NoVFI episodes, cycle 2 could be divided into 2 distinct subgroups. Subgroup 1 (n=7) had a short ICI, long WCT, and same REA as cycle 1. Subgroup 2 (n=6) had a long ICI, short WCT, and different REA than cycle 1.

ICIs in subgroup 1 were all shorter than 200 ms (142±27 ms), but were all longer than 400 ms (672±228 ms) in subgroup 2 (P<0.002). While the cycle 2 ICI of subgroup 1 was not different from that in the VFI episodes, in subgroup 2 it was significantly longer than in the VFI episodes (P<0.002). Subgroup 1 all had WCTs longer than 100 ms (135±21 ms), while subgroup 2 all had WCTs shorter than 80 ms (56±12 ms, P<0.01). WCTs of both subgroups were significantly shorter than WCTs of cycle 2 in VFI episodes (P<0.004).

Cycle 2 SEA repeatability in subgroup 1 (63±48%) was different (P<0.04) from subgroup 2 (0±0%) in NoVFI episodes. Cycle 2 SEA repeatability in VFI episodes (60±33%) was different from that of subgroup 2 (P<0.007), but not subgroup 1. Thus, cycle 2 SEAs in the NoVFI subgroup with longer ICIs (subgroup 2) moved to a different site, whereas in the NoVFI subgroup with shorter ICIs (subgroup 1), as well as in VFI episodes, they mostly remained in the REA of cycle 1. The mean dV/dt for cycle 2 in VFI episodes also differed from that of subgroup 2 (−3.2±1.7 V/s), but not of subgroup 1 (−2.2±0.6 V/s) in the NoVFI episodes.

Thus, episodes could be distinctly divided into 3 groups: 1) VFI, 2) NoVFI subgroup 1, and 3) NoVFI subgroup 2. The propagation patterns (FIG. 11) as well as electrograms (FIG. 12) of cycle 1 from these 3 groups were nearly identical. Cycle 2 for groups 1 and 2 were also similar but not quite identical (FIG. 11). Group 3 had a different REA and shorter WCT than groups 1 and 2.

III. Discussion

Similarity of First Postshock Cycle Regardless of Shock Outcome.

Our major finding is that the first cycle following a $ULV_{50}$ shock that induces VF cannot be distinguished from that following a shock of identical strength and timing that does not induce VF. This finding was apparent in the activation sequence animations and in the similarity of the following first cycle variables: 1) SEA repeatability, 2) postshock interval, 3) WCT, 4) dV/dt at the SEA, 5) similarity function and 6) temporal lag.

Most studies reporting differences of activation sequences and dispersion of refractoriness between VFI and NoVFI episodes used multiple shock strengths and coupling intervals (Kirchhof P F, et al., *Basic Res Cardiol.* 1997;92:35–44; Kuo C S et al., In: Zipes D P,Jalife J, eds. *Cardiac Electrophysiology and Arrhythmias.* Orlando: Grune and Stratton: 1985:277–285). Those studies found that NoVFI episodes correlated with a lower dispersion of refractoriness immediately after the shock, whereas VFI episodes correlated with a greater dispersion of refractoriness. However, in those studies the shock strengths of NoVFI episodes were higher than those of VFI episodes. Thus, absence of VF induction may not have been secondary to a lower dispersion of refractoriness; rather, both lack of VF induction and a lower dispersion of refractoriness could have been secondary to higher shock strength. To evaluate this possibility, we kept shock strength and timing constant. Our results suggest that when shock strength and timing are constant, differences in the dispersion of refractoriness are not large enough to cause measurable differences in postshock activation sequences and potentials. However, differences may exist immediately after the shock that are too small to be detected. These very small differences, according to Chaos theory (Kaplan D T et al., *J Cardiovasc Electrophysiol.* 1991;2:342–354), could cause prominent differences after several cycles.

Association of Overlapping Cycles With VFI.

Although differences between VFI and NoVFI episodes were first seen at cycle 2, a prominent distinction was not universally seen until cycle 3. This is because cycle 2 in one NoVFI subgroup behaved similarly to cycle 2 in the VFI episodes. However, no overlapping cycles were present in either NoVFI subgroup whereas they were always present in the VFI group. Overlapping cycles may not be the direct cause of VF induction, but may be a marker for short ICIs and long WCTs that are responsible for unstable reentry and VF induction. However, these results imply that at least 3 ectopic cycles with overlap by the third cycle may be required to initiate VF. If so, a method to halt the initiation of ectopic cycles in the REA could prevent VF even if it is applied as late as the third postshock cycle. Recent defibrillation (KenKnight BH et al., *Pacing and Clin Electrophys.* 1998;21:806) and VF induction studies (KenKnight BH et al., *Pacing and Clin Electrophys.* 1998;21:806) support this hypothesis.

The foregoing is illustrative of the present invention, and is not to be construed as limiting thereof. The invention is defined by the following claims, with equivalents of the claims to be included therein.

We claim:

1. A method for predicting the outcome of arrhythmia therapy in a subject in need thereof, comprising the steps of:
   (a) detecting an arrhythmia in the heart of a subject;
   (b) delivering a first arrhythmia therapy pulse to the heart of said subject; and then
   (c) determining the presence or absence of overlapping cycles in the heart of said subject, the presence of overlapping cycles indicating that said first arrhythmia therapy pulse did not successfully treat said arrhythmia.

2. A method according to claim 1, wherein said determining step is carried out within the first ten cardiac cycles following said first arrhythmia therapy pulse.

3. A method according to claim 1, wherein said determining step is carried out within the first three cardiac cycles following said first arrhythmia therapy pulse.

4. A method according to claim 1, further comprising the step of:
   (d) delivering a second arrhythmia therapy pulse if overlapping cycles are determined.

5. A method according to claim 4, wherein said second arrhythmia therapy pulse is delivered within one second of detecting said overlapping cycles.

6. A method according to claim 1, wherein said arrhythmia is an atrial arrhythmia, and said first arrhythmia therapy pulse is an atrial arrhythmia therapy pulse.

7. A method according to claim 1, wherein said arrhythmia is an atrial fibrillation, and said first arrhythmia therapy pulse is an atrial defibrillation pulse.

8. A method according to claim 1, wherein said arrhythmia is an ventricular arrhythmia, and said first arrhythmia therapy pulse is a ventricular arrhythmia therapy pulse.

9. A method according to claim 1, wherein said arrhythmia is a ventricular fibrillation, and said first arrhythmia therapy pulse is a ventricular defibrillation pulse.

10. A method according to claim 1, wherein said arrhythmia therapy pulse comprises a single electrical shock.

11. A method according to claim 1, wherein said arrhythmia therapy pulse comprises a biphasic exponential waveform shock.

12. A method according to claim 1, wherein said arrhythmia therapy pulse comprises a plurality of electrical shocks.

13. A method for predicting the outcome of arrhythmia therapy in a subject in need thereof, comprising the steps of:
   (a) detecting an arrhythmia in the heart of a subject;
   (b) delivering a first arrhythmia therapy pulse to the heart of said subject; and then
   (c) determining the presence or absence of overlapping cycles in the heart of said subject, the presence of overlapping cycles indicating that said first arrhythmia therapy pulse did not successfully treat said arrhythmia;
   wherein said determining step is carried out by calculating an overlapping cycle index.

14. A method according to claim 13, wherein said overlapping cycle index is calculated from the wavefront conduction time of a given cycle and the intercyle interval of the cycle subsequent to said given cycle.

15. A method according to claim 14, wherein said given cycle is within the first ten cardiac cycles following said first arrhythmia therapy pulse.

16. A method according to claim 13, wherein said determining step is carried out within the first ten cardiac cycles following said first arrhythmia therapy pulse.

17. A method according to claim 13, wherein said determining step is carried out within the first three cardiac cycles following said first arrhythmia therapy pulse.

18. A method according to claim 13, further comprising the step of:
   (d) delivering a second arrhythmia therapy pulse if overlapping cycles are detected.

19. A method according to claim 18, wherein said second arrhythmia therapy pulse is delivered within one second of detecting said overlapping cycles.

20. A method according to claim 13, wherein said arrhythmia is an atrial arrhythmia, and said first arrhythmia therapy pulse is an atrial arrhythmia therapy pulse.

21. A method according to claim 13, wherein said arrhythmia is an atrial fibrillation, and said first arrhythmia therapy pulse is an atrial defibrillation pulse.

22. A method according to claim 13, wherein said arrhythmia is an atrial arrhythmia, and said first arrhythmia therapy pulse is an atrial arrhythmia therapy pulse.

23. A method according to claim 13, wherein said arrhythmia is a ventricular fibrillation, and said first arrhythmia therapy pulse is a ventricular defibrillation pulse.

24. A method according to claim 13, wherein said arrhythmia therapy pulse comprises a single electrical shock.

25. A method according to claim 13, wherein said arrhythmia therapy pulse comprises a biphasic exponential waveform shock.

26. A method according to claim 13, wherein said arrhythmia therapy pulse comprises a plurality of electrical shocks.

27. An apparatus for delivering an arrhythmia therapy pulse to a subject in need thereof and rapidly predicting the outcome of said arrhythmia therapy, said apparatus comprising:
 (a) a detector for detecting an arrhythmia in the heart of a subject;
 (b) a therapy pulse generator operatively associated with said detector for delivering a first arrhythmia therapy pulse to the heart of said subject; and
 (c) determining means for determining the presence or absence of overlapping cycles in the heart of said subject following said first arrhythmia therapy pulse, the presence of overlapping cycles indicating that said first arrhythmia therapy pulse did not successfully treat said arrhythmia.

28. An apparatus according to claim 27, further comprising:
 (d) means operatively associated with said determining means and said therapy pulse generator for triggering the delivery of a second arrhythmia therapy pulse by said therapy pulse generator if overlapping cycles are detected.

29. An apparatus according to claim 27, wherein said apparatus is an implantable cardioverter defibrillator.

30. An apparatus according to claim 27, wherein said determining means comprises a microprocessor.

31. An apparatus according to claim 27, wherein said therapy pulse generator includes a battery and a capacitor operatively associated with said battery.

32. An apparatus according to claim 27, further comprising a housing, wherein said detector, said therapy pulse generator, and said determining means are contained within said housing.

33. An apparatus according to claim 27, further comprising a defibrillation electrode formed on the outer surface of said housing.

* * * * *